United States Patent
Smith et al.

(10) Patent No.: US 9,561,196 B2
(45) Date of Patent: Feb. 7, 2017

(54) METHODS FOR EVALUATING AND IMPLEMENTING PROSTATE DISEASE TREATMENTS

(75) Inventors: Gary J. Smith, Buffalo, NY (US); Howard M. Reisner, Durham, NC (US); Danny R. Gray, Charlottesville, VA (US); Wendy Huss, Kenmore, NY (US)

(73) Assignee: Health Research, Inc., Buffalo, NY (US)

( * ) Notice: Subject to any disclaimer, the term of this patent is extended or adjusted under 35 U.S.C. 154(b) by 1316 days.

(21) Appl. No.: 13/230,317

(22) Filed: Sep. 12, 2011

(65) Prior Publication Data

US 2012/0115781 A1 May 10, 2012

Related U.S. Application Data

(63) Continuation-in-part of application No. 12/011,929, filed on Jan. 30, 2008, now Pat. No. 8,048,640.

(60) Provisional application No. 60/898,332, filed on Jan. 30, 2007, provisional application No. 61/381,551, filed on Sep. 10, 2010.

(51) Int. Cl.

| | | |
|---|---|---|
| A61K 31/03 | (2006.01) | |
| A61K 31/04 | (2006.01) | |
| A61K 31/055 | (2006.01) | |
| A61K 31/095 | (2006.01) | |
| A61K 31/122 | (2006.01) | |
| A61K 31/24 | (2006.01) | |
| A61K 31/4164 | (2006.01) | |
| A61K 38/09 | (2006.01) | |
| A61K 31/164 | (2006.01) | |
| A61K 31/337 | (2006.01) | |
| A61K 31/56 | (2006.01) | |
| G01N 33/50 | (2006.01) | |
| G01N 33/574 | (2006.01) | |

(52) U.S. Cl.
CPC .......... *A61K 31/164* (2013.01); *A61K 31/337* (2013.01); *A61K 31/4164* (2013.01); *A61K 31/56* (2013.01); *G01N 33/5011* (2013.01); *G01N 33/5088* (2013.01); *G01N 33/57434* (2013.01); *G01N 2800/342* (2013.01)

(58) Field of Classification Search
CPC ...... A61K 31/03; A61K 31/04; A61K 31/045; A61K 31/055; A61K 31/095; A61K 31/122; A61K 31/136; A61K 31/165; A61K 31/277; A61K 31/4164; A61K 31/4166; A61K 38/09
See application file for complete search history.

(56) References Cited

PUBLICATIONS

American Cancer Society; cancer.org/acs/groups/cid/documents/webcntent/002995-pdf.pdf; 2015 Copyright American Cancer Society; downloaded Feb. 8, 2016.*
Pienta, K.J., Seminars in Oncology, 28(4), Suppl 15: pp. 3-7, 2001.*
Nelius, T., et al. BJU International, 98: 580-585, 2006.*
Noguchi, M. et al., International Journal of Urology, 11: 103-109, 2004.*
Sato, et al., Neoplasia, 7(9): 838-846, 2005.
Huss et al., The Prostate, 60: 77-90, 2004.
Presnell et al., American Journal of Pathology, 159(3); 855-860, 2001.
Singh et al., Cancer Epidemiology, Biomarkers & Prevention, 12: 933-939, 2003.
Gray et al., Short-Term Human Prostate Primary Xenografts: An in Vivo Model of Human Prostate Cancer Vasculature and Angiogenesis, Cancer Research 64, 1712-1721. Mar. 1, 2004.

* cited by examiner

*Primary Examiner* — Misook Yu
*Assistant Examiner* — Anne Holleran
(74) *Attorney, Agent, or Firm* — Hodgson Russ LLP

(57) ABSTRACT

Provided is a method for evaluating test agents as candidates for treating prostatic diseases, including benign prostatic hyperplasia and androgen dependent and androgen independent prostate cancer. The method comprises providing a mouse comprising a human prostate primary xenograft, where the xenograft contains blood vessels that include human endothelial cells, initiating androgen deprivation in the mouse, administering to the mouse a test agent within a period of 1-7 days after initiating the androgen deprivation, and determining a reduction in human epithelial cells in the xenografts and/or a reduction in number of the endothelial cells or blood vessels in the xenograft. Also provided is a method for treating an individual for human prostate cancer or benign prostatic hyperplasia. The method comprises initiating androgen deprivation in the individual and administering to the individual an agent capable of inducing apoptosis of vascular endothelial cells within a period of 1-7 days of initiating androgen deprivation.

3 Claims, 17 Drawing Sheets

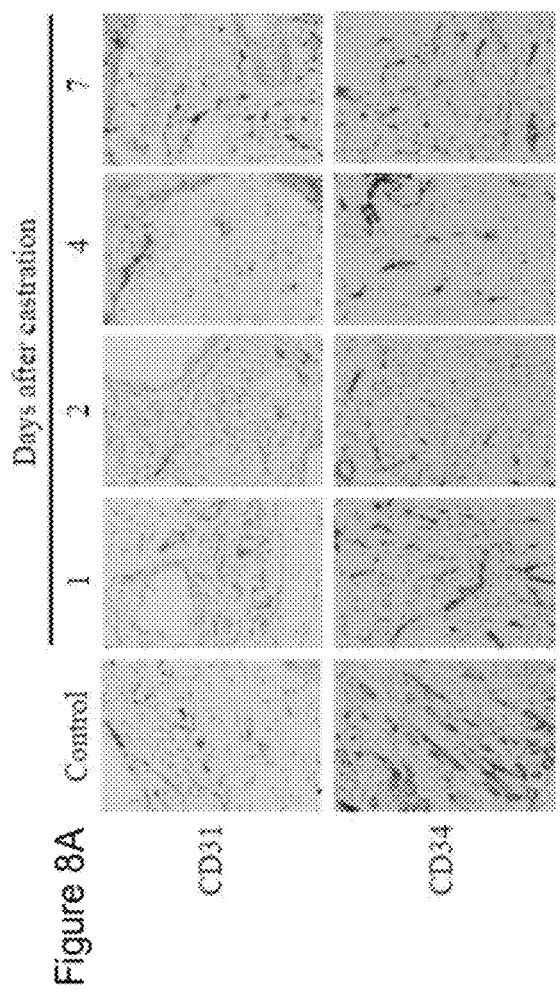
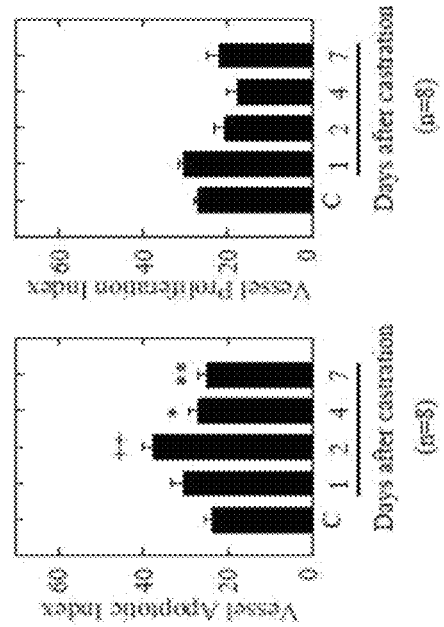
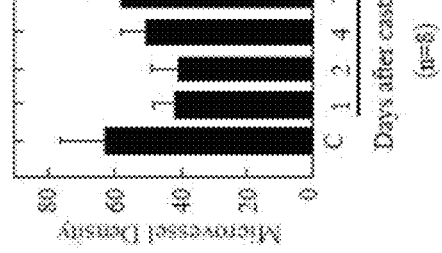

METHODS FOR EVALUATING AND IMPLEMENTING PROSTATE DISEASE TREATMENTS

This application claims priority to U.S. Application Ser. No. 61/381,551, filed Sep. 10, 2010, and is a continuation-in-part of U.S. application Ser. No. 12/011,929, which in turn claims priority to U.S. Application Ser. No. 60/898,332, filed Jan. 30, 2007, the disclosures of each of which are incorporated herein by reference.

This work was supported by funding from the National Institutes of Health grant no. P01-CA7739-04 and Department of Defense grant no. PC030689. The Government has certain rights in the invention.

FIELD OF THE INVENTION

The invention relates generally to prostatic diseases, and specifically to methods for treating prostatic disease and identifying agents for treating prostatic disease.

DESCRIPTION OF RELATED ART

The major cause of morbidity and mortality from prostate cancer is the result of androgen-independent metastatic tumor growth. However, advanced prostate cancer is often treated by androgen deprivation therapy, and after initial response, most prostate cancers become hormone-refractory and eventually lethal. Current therapeutic approaches have not been able to treat androgen deprivation resistant tumors. This is at least in part due to the lack of valid methods for evaluating prostate disease etiology and therapeutic approaches in animal models. Thus, there is an ongoing need to develop improved methods for evaluating potential anti-cancer agents and treatment modalities in animal systems that closely model human prostate disease.

SUMMARY OF THE INVENTION

The present invention provides a method for evaluating test agents as candidates for treating prostatic diseases, including benign prostatic hyperplasia (BPH) and androgen dependent and androgen independent prostate cancer. The method comprises providing a mouse comprising a human prostate primary xenograft, wherein the xenograft comprises blood vessels that contain human endothelial cells, initiating androgen deprivation in the mouse, administering to the mouse a test agent within a period of 1-7 days after initiating the androgen deprivation, and determining a reduction in human epithelial cells in the xenografts and/or a reduction in number of the endothelial cells/blood vessels in the xenograft. A reduction of human epithelial and/or human endothelial cells in the xenograft and/or a reduction in the number of blood vessels in the xenograft compared to a xenograft in a control mouse is indicative that the agent is a candidate for treating human prostate cancer or prostatic hyperplasia.

Also provided is a method for treating an individual for human prostate cancer or benign prostatic hyperplasia. The method comprises initiating androgen deprivation in the individual and administering to the individual an agent capable of inducing apoptosis of vascular endothelial cells within a period of 1-7 days of initiating androgen deprivation. This is expected to induce apoptosis of vascular endothelial cells that are exposed due to androgen deprivation. It is believed that death of the vascular endothelial cells leads to vascular leakage and ultimately to death of the prostate epithelial cells, which in turn results in the death of the diseased tissue.

BRIEF DESCRIPTION OF THE FIGURES

FIG. 8A provides a photographic representation of CD31 and CD34 staining of vessels before and after castration. The study was performed over seven days following castration (removal of the supply of androgen) on Day 0. The results demonstrate that, regardless of the marker, the number of small human blood vessels decreased over the initial two days following castration, and rebounded to nearly the starting levels by Day 7. FIGS. 8B-8D provide graphical representations of changes in MVD, vessels apoptotic index, vessel proliferation index, and testosterone levels (nM), respectively, post-castration. The vessel apoptotic index refers to the fraction of vessels that contain at least a single endothelial cell that is undergoing apoptosis in response to androgen deprivation. The peak of cell death is concurrent with the time of observation of the minimal number of vessels in FIG. 8A.

DETAILED DESCRIPTION OF THE INVENTION

Figure 1:
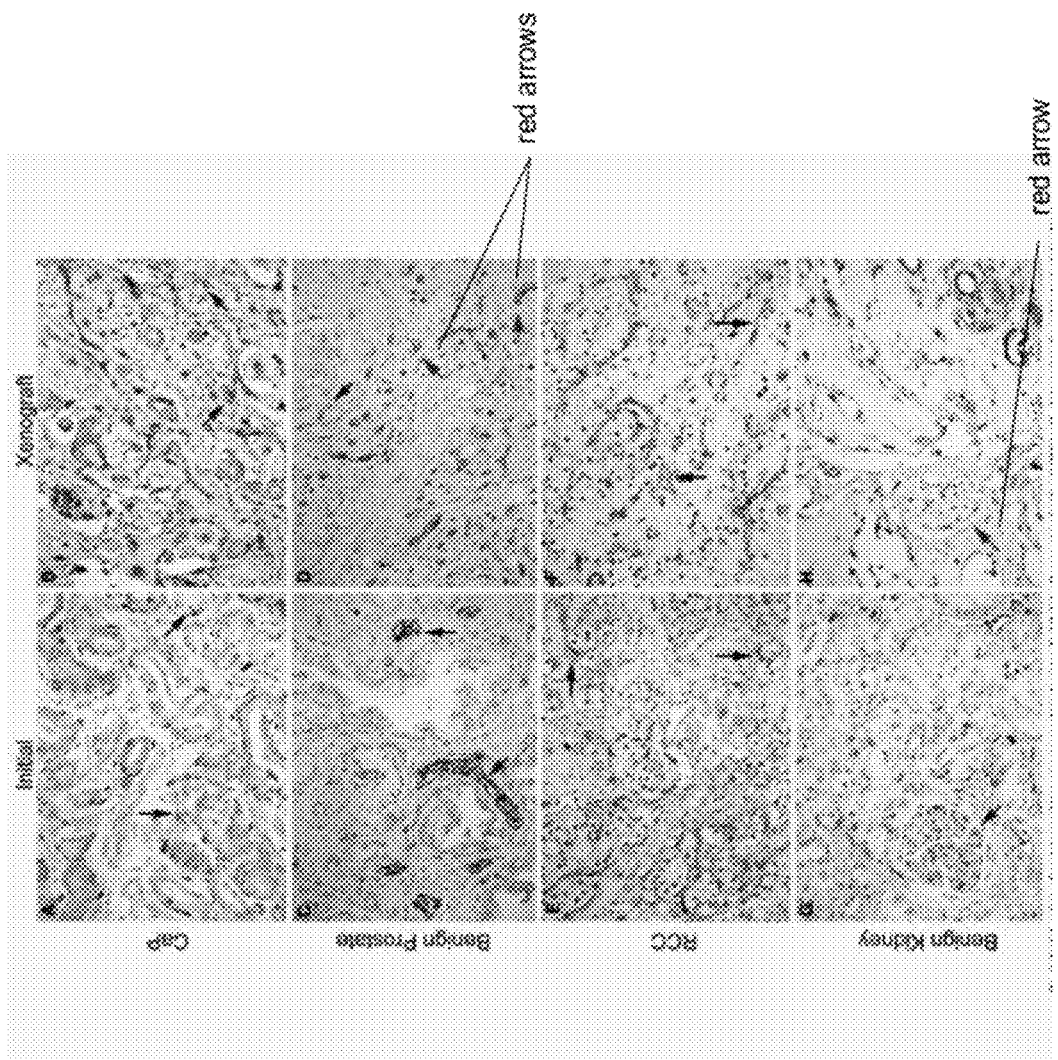
FIG. 1 provides a photographic representation of spatial analysis of prostate vasculature using immunohistochemistry (IHC). Endothelial cells were stained with human specific anti-CD31 antibody to analyze the architectural relationship of histological structures (e.g., prostate glands and kidney glomeruli) and images captured at ×200. Panels A and B, CaP (arrows indicate stained vessels). Panels C and D, benign prostate (black arrows indicate vessels near glands, and red arrows indicate vessels in the stroma). Panels E and F, RCC (arrows indicate stained vessels). Panels G and H, benign kidney (black arrow indicates a normal glomerulus, and red arrow indicates an atrophic glomerulus).

The vasculature of the human prostate is unique among organs that are major sites of human disease in that the endothelial compartment appears significantly less stable than the vascular compartment of other organs. The epithelial compartment of the prostate demonstrates a proliferative index as much as two orders of magnitude greater than other organs and as much as 50-70% of the small vessels in benign and malignant prostate lack association with vascular smooth muscle cells that signify vascular maturation and stability. The present invention takes advantage of a mouse model of prostate disease that closely replicates this human prostatic microenvironment. In particular, the invention employs mice that have xenografts that contain vasculature that is predominantly comprised of human cells, as evidenced by analysis of xenografts using species-specific antibodies which reveal that the percentage of human vessels in the prostate xenografts at one month after implantation is greater than 80%. Further, murine vessels are confined mainly in a compressed connective tissue layer at the periphery of the xenografts. Thus, the present invention provides a system for evaluating chemotherapeutic agents as candidates for treatment of human prostate disease that can exploit newly discovered effects of androgen deprivation on human prostatic vasculature. In this regard, our data in human prostate xenografts transplanted to immunocompromised mouse hosts demonstrate that the endothelial cells of the human vasculature express androgen receptor, demonstrate a peak of apoptotic death at two days after androgen deprivation therapy, and disruption of the endothelial cells causes the vessels to leak plasma components into the interstitial space. The death of the endothelial compartment is followed by apoptotic death of the glandular epithelial compartment at 6-7 days after androgen deprivation. However, in response to the hypoxia induced by the rapid vascular involution, proliferation of the endothelial compartment with revascularization of the prostate tissue begins between 4 and 7 days after androgen-deprivation. Thus, the present invention is based on the discovery that the period between 1 and 7 days, and optimally between 1 and 4 days after androgen deprivation, represents an important but transient window for identifying agents that can inhibit revascularization of the prostate and/or deliver adjuvant therapies to areas of labilized vasculature where they may have improved access to prostate cancer/epithelial cells. This window has not been previously exploited, and treatment modalities have been delayed allowing maturation and stabilization of the neovasculature, minimizing the response to adjuvant therapy.

It is expected that inhibition of revascularization of the prostate tissue microenvironment during the transient window of prostate vasculature labialization will make permanent the tissue destruction caused by androgen deprivation and the hypoxia induced by the vascular regression, resulting in death of the mesenchymal as well as the benign/malignant epithelial compartment. The use of transient androgen deprivation to labilize specifically the prostatic vasculature is therefore a novel aspect of this invention.

The invention accordingly takes advantage of these observations to provide a method for identifying agents that can target the prostate vasculature during a transient interval of revascularization induced by androgen deprivation, when the endothelial compartment is proliferatively active and not associated with the stabilizing/protective mural cell cells, rather than attempting to interdict the stable vasculature, which is an approach that has proven largely ineffective in many tumor models. The method comprises the steps of providing a mouse that is compared to a control mouse. Thus, the mouse that is compared to the control mouse can be considered a test mouse. The test mouse comprises a test human prostate primary xenograft, wherein the test human prostate primary xenograft comprises test blood vessels which contain test human endothelial cells. Androgen deprivation is initiated in the test mouse and a control mouse, and a test agent is administered to the test mouse within a period of 1-7 days after initiating the androgen deprivation. It is considered that a reduction of endothelial cells in the test xenograft and/or a reduction in the number of test blood vessels compared to a control xenograft in a control mouse is indicative that the agent is a candidate for treating human prostate cancer or benign prostatic hyperplasia. The test agent can be administered before, at and/or during any period within the 1-7 day period after initiation of androgen deprivation therapy. In one embodiment, the test agent is not 2-Methoxyestradiol (2-ME).

Figure 6:
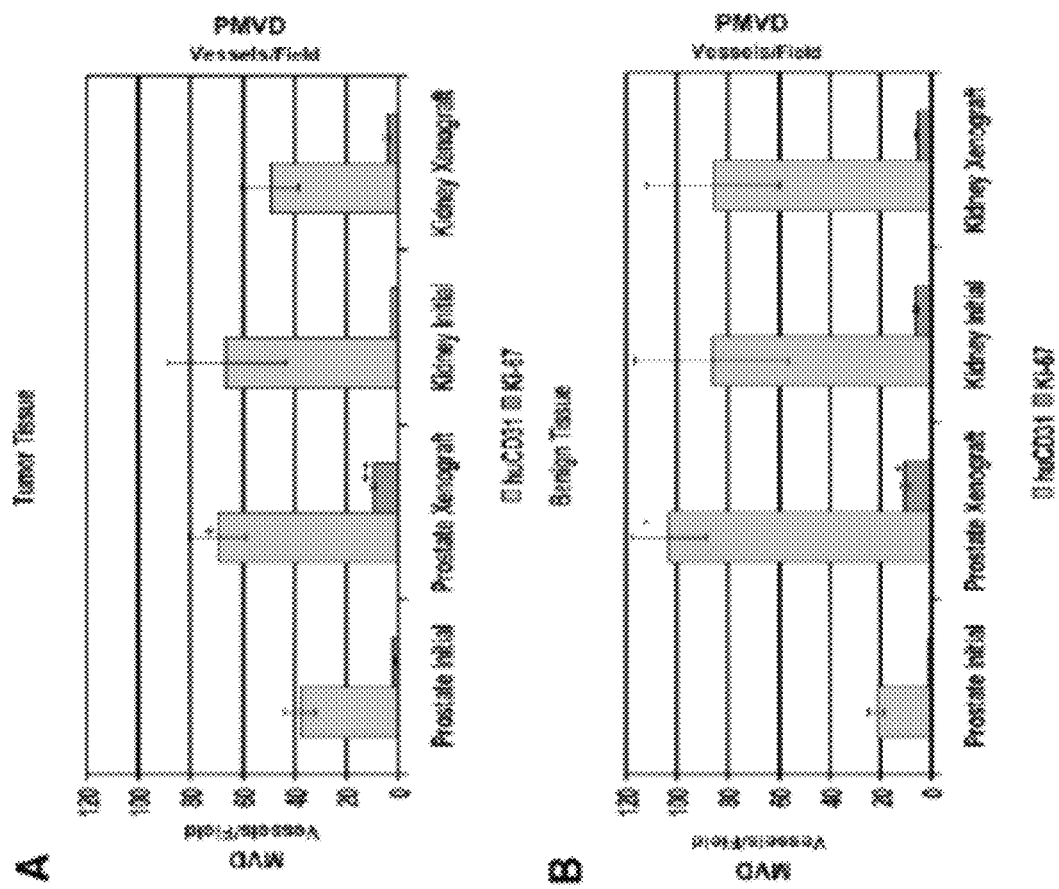
FIG. 6 provides a graphical representation of quantification of vasculature in prostate and kidney represented as number of vessels per field (MVD) and number of vessels with proliferating endothelial cells per field (PMVD) in benign and tumor specimens by organ and growth condition, initial tissue, and xenograft. Panel A, tumor tissue: prostate (CD31, n=14, +, P=0.009; Ki-67, n=14, ++, P<0.001); kidney (CD31, n=5, P>0.05; Ki-67, n=5, P>0.05). Panel B, benign tissue: prostate (CD31 and Ki-67, n=22, *, P<0.001); kidney (CD31, n=4, P>0.05; Ki-67, n=2, P>0.05). Data shown are means; bars, SE.

It will be apparent to those skilled in the art that the control mouse to which the effects of the test agent in the test mouse can be compared comprises a human prostate primary control xenograft, and that the control xenograft comprises control blood vessels, and that the control blood vessels comprise control human vascular endothelial cells and control human epithelial cells. Thus, in one embodiment, the invention provides a method for identifying a test agent as a candidate for treating human prostate cancer or benign prostatic hyperplasia which comprises i) providing a test mouse, wherein the test mouse comprises a human prostate primary test xenograft, wherein the test xenograft comprises test blood vessels, wherein the test blood vessels comprise test human vascular endothelial cells and test human epithelial cells;

ii) providing a control mouse, wherein the control mouse comprises a human prostate primary control xenograft, wherein the control xenograft comprises control blood vessels, wherein the control blood vessels comprise control human vascular endothelial cells and control human epithelial cells, iii) initiating androgen deprivation in the test mouse and the control mouse;

iv) administering to the test mouse the test agent within a period of 1-7 days after initiating the androgen deprivation;

v) determining in the test mouse from iii) a reduction in number of test blood vessels and/or test human endothelial cells and/or test human epithelial cells in the xenograft;

vi) at a time point between 1 and 7 days after initiating androgen deprivation in the control mouse observing a reduction in number of the control blood vessels and/or the control human endothelial cells and/or the control human epithelial cells in the xenograft;

wherein a reduction in number of the test blood vessels and/or the test vascular endothelial cells and/or the test epithelial cells in the test xenograft relative to the control xenograft in the control mouse to which the agent has not been administered is indicative that the test agent is a candidate for treating human prostate cancer or prostatic hyperplasia in an individual. In one embodiment, step vi) comprises observing a reduction in the control endothelial cells. This is distinct from previously published results which analyzed the effects of androgen deprivation on human prostate tumors in mice and showed that androgen deprivation alone does not affect endothelial cells (see, for example, Sato et al., Neoplasia (2005) pp 838-846, and FIG. 6 therein).

The method for treating an individual for human prostate cancer or BPH comprises initiating androgen deprivation in the individual and administering to the individual an agent capable of inducing apoptosis of vascular endothelial cells, or epithelial cells, within a period of 1-7 days of initiating androgen deprivation, wherein the administration of the agent results in the death of vascular endothelial cells in the prostate of the individual and/or reduces the number of blood vessels in the prostate of the individual. This transient androgen deprivation approach (i.e., less than 2 weeks of androgen deprivation) is expected to provide two important clinical benefits. First, transient pharmacologic androgen deprivation can minimize/prevent the many detrimental side effects of long-term androgen deprivation, including: loss of muscle mass, gynecomastia, weight gain and impotence/loss of libido. Second, transient pharmacologic androgen deprivation would allow cyclic treatment regimes, each capitalizing on the maintenance of androgen sensitivity of the benign endothelial cell compartment. While not intending to be bound by any particular theory, it is considered that the death of endothelial cells induced by androgen deprivation will perturb the normal function of the endothelial cell barrier which would functionally actively exclude therapeutic drugs from entering the prostate tissue and therefore prevent the drugs from inducing death of prostate cancer epithelial cells. Prostate epithelial cells are epithelial cells of a benign gland (or a gland characterized by BPH). Cancer epithelial cells are the malignantly transformed version of benign epithelial cells. Prostate epithelial cells are preferably killed or reduced in number to alleviate BPH, while prostate cancer epithelial cells are preferably killed or reduced in number in treatment of prostate cancer.

One example of an agent capable of inducing apoptosis of vascular endothelial cells, prostate epithelial cells, and prostate cancer epithelial cells is taxotere. Taxotere is a semi-synthetic anticancer agent derived from *Taxus baccata*. It has shown a wide spectrum of cytotoxicity for various solid tumors as well as clinical activity when used for the treatment of breast, lung, ovarian, and prostate cancers, and may have pleiotropic effects on human cancers. However, taxotere is not conventionally administered in temporal proximity with androgen deprivation therapy.

Androgen deprivation can be achieved in a variety of ways known to those skilled in the art. For example, orchiectomy (castration) may be performed to inhibit endogenous androgen production by the testes. Additionally, various anti-androgenic agents are known in the art to inhibit androgen production. For example, luteinizing hormone-releasing hormone (LHRH) analogs, such as leuprolide, goserelin or triptorelin, or commercially available LHRH antagonists may be administered by conventional means. Further, antiandrogens, such as flutamide, bicalutamide, and nilutamide, or other androgen-suppressing drugs, such as estrogens, may be administered. The androgen deprivation may be intermittent or continuous, and may be initiated before, during or after administration of an agent that causes death of endothelial cells or is being evaluated for the ability to cause death of endothelial cells. Further, the agent can be administered with additional conventional chemotherapeutic agents and/or radiation therapy. Radiation may be delivered either via external beam radiotherapy or via local placement of radioactive seeds within the prostate (brachytherapy). The agent can be administered with conventional chemotherapeutic agents or radiation therapy concurrently or sequentially. The method of the invention is expected to also be useful for identifying agents for use in inhibiting the aberrant enlargement of the prostate characteristic of BPH.

The agents can be formulated in pharmaceutically acceptable carriers to obtain pharmaceutical compositions for use in the methods of the invention. The pharmaceutical compositions can be delivered by any suitable administration route, such as parenteral, e.g., intravenous, intradermal, subcutaneous, oral (e.g., inhalation), transdermal (topical), transmucosal, and rectal administration, or by direct injection into the prostate or xenograft.

Without intending to be bound by any particular theory, the invention is believed to exploit the creation/unmasking of unique targets associated with damage to the human prostate vascular network by androgen deprivation, and in particular the following newly discovered effects of androgen deprivation in human prostate tissue as observed in the xenografts described herein:

1. Microvessel density (MVD), the percentage of vessels with proliferatively active endothelial cells, and expression of androgen receptor (AR) in human endothelial cells decreases rapidly after androgen deprivation, reaches a nadir on Day 2 after androgen deprivation, and increases markedly between Days 4 and 7 in the human prostate primary xenografts
2. Apoptotic cell death in human endothelial cells peaks on Day 2, and decreases over Days 4-7 after androgen deprivation.
3. Expression of VEGF, VEGR-2, BFGF and PDGF-BB protein increases in endothelial cells after androgen deprivation, peaking between Days 2-4 after androgen deprivation, and decreases over Days 4-7.
4. Tissue factor is not expressed in endothelial cells in human prostate primary xenografts at one month post-implantation, however, expression in endothelial cells is increased markedly in response to androgen deprivation, indicating endothelial cell damage.
5. Androgen deprivation induces intravascular and perivascular deposition of fibrin/fibrinogen in the human prostate primary xenografts, indicating endothelial cell damage.

Taken together, these observations indicate that the rapid reduction and recovery of MVD following androgen deprivation means that the reduction in MVD is not due involution of the vasculature, but rather due to death of the endothelial cells in response to the loss of androgen and that the recovery is not due to angiogenesis, but rather to re-endothelialization of the denuded vascular channels. This reasoning provides a rationale for why purely anti-angiogenic agents/modalities have had such limited success in the treatment of the mature vasculature of tumors. Further, it is believed that androgen-deprivation will unmask/create transiently unique targets in the vasculature, and likely in the interstitial tissue due to destruction of the endothelial permeability barrier because of death of the prostate endothelial cells. However, the rapid re-endothelialization will result in the loss of these targets. Accordingly, it is expected that creation/unmasking of these unique targets will produce sensitivity to agents that not only target endothelial cells, but also in the stromal and epithelial compartments, and on the vascular basement membrane.

In addition to the foregoing, we demonstrate that increased VEGF-A expression in human prostate endothelial cells precedes vascular recovery after androgen deprivation.

The following Examples are meant to illustrate particular embodiments of the invention and are not meant to be limiting.

Example 1

This Example demonstrates making human prostate primary xenografts to provide an in vivo model of human prostate cancer vasculature and angiogenesis, wherein the xenografts comprise blood vessels, and wherein the blood vessels contain a preponderance of human endothelial cells.

In this Example, angiogenesis in human kidney primary xenografts established from human renal cell carcinoma (RCC) and non-involved kidney tissue, a highly vascular organ and cancer, was compared to angiogenesis in xenografts from the relatively less vascularized prostate. Immunohistochemical identification of the human versus mouse host origin of the endothelial cells, and of human endothelial cell proliferation, in the human prostate and human kidney xenografts demonstrated: 1) the majority of the vessels in primary xenografts of benign and malignant tissue of both organs were lined with human endothelial cells; 2) The mean vessel density (MVD) was increased in both the CaP and benign prostate xenografts relative to the initial tissue, while there was no significant difference in MVD in the RCC and benign kidney xenografts compared to the initial tissue; and 3) The number of vessels with proliferating endothelial cells in primary xenografts of CaP and benign prostate increased compared to their respective initial tissue specimens, while the number of vessels with proliferating endothelial cells decreased in the benign kidney xenografts. Primary human prostate xenografts (therefore, represent a valuable in vivo model for the study of human angiogenesis within a human tissue microenvironment and for comparison of angiogenesis in CaP versus benign prostate. Consequently, the unique interaction of the prostate vasculature with the prostate tissue microenvironment is maintained in the primary xenografts and provides a valuable model for evaluating agents for targeting newly discovered properties of human angiogenesis and neovascularization in CaP.

To obtain and analyze the data as presented herein, the following materials and procedures were employed.

All experimentation involving laboratory animals was performed in accordance with the National Institutes of Health guidelines and approved by the Institutional Animal Care and Use Committee at the University of North Carolina at Chapel Hill. Male athymic nude mice, three months of age, (Hsd: athymic Nude/Nude, Harlan Sprague-Dawley, Indianapolis, Ind.) that were to be hosts for prostate xenografts were implanted subcutaneously with 12.5 mg sustained-release testosterone pellets (Innovative Research of America, Sarasota, Fla.) before transplantation of the prostate tissue to maintain serum testosterone levels in the host at ~4 ng/ml throughout the study, mimicking human serum levels. Mouse hosts for kidney xenografts also were implanted with testosterone pellets.

Tissue Collection, Cryopreservation, Implantation and Harvest

All surgically resected tissues were collected in accordance with National Institutes of Health guidelines on the use of human subjects, with approval by the IRB at UNC Hospitals. Human tissue designated as excess prostate and kidney tissue was obtained from 42 and 10 patients, respectively, at the time of prostatectomy or nephrectomy. Gross morphological assessment of the resected organ/tumor by the surgeons was the basis for identification of the specimens as originating in non-involved (benign, B) or tumor (T) areas. Resected tissue specimens samples were submerged immediately in iced ViaSpan solution (Barr Laboratories Inc., Pomona, N.Y.), and transported on ice for transplantation or processing. An initial tissue (IT) specimen, at least 3 mm$^3$, was cut from each tissue sample, placed in 10% formalin for fixation and paraffin-embedded. Xenografts were established from tissue as described [1]. Briefly, the remainder of each tissue specimen was cut into wedge-shaped pieces 2-3 mm in length and 1-2 mm in width at the broadest end and the wedges were transplanted immediately, or were cryopreserved in prostate growth media (Richter's MEM, 2% Fetal Bovine Serum, 1% Antibiotic-Antimycotic Solution, 0.1% ITS, 0.1% EGF, 0.12% Nicotinamide by volume/weight) with 10% dimethyl sulfoxide at −140° C. [2]. Frozen tissue wedges were prepared for transplantation by thawing on ice and rinsing 3× in sterile ViaSpan. For implantation, small (~3 mm) incisions were made in the skin on the right and left flanks of an athymic nu/nu mouse anesthetized with Domitor (Pfizer, Inc., New York, N.Y.), tissue wedges to be implanted were dipped in Matrigel™ (BD Biosciences, Bedford, Mass.) and the tissue was inserted into the subcutaneous space through a 10 gauge trocar device (Popper & Sons. Inc., Lincoln, R.I.). Between 3 and 10 wedges from a single patient were implanted through a individual incisions along each flank. Incision sites were closed with Nexband tissue glue (Veterinary Products Laboratories, Phoenix, Ariz.). Mice were observed weekly after implantation. One month post-implantation, the host mice were euthanized and the xenografts harvested, placed in 10% formalin for fixation and paraffin-embedded. Paraffin blocks were sectioned (5 μm) onto ProbeOn Plus slides (Fisher Scientific International, Suwanee, Ga.).

Tissue Evaluation

A histologic section from each initial tissue specimen, and each xenograft specimen, was stained with Hematoxylin and Eosin for definitive identification and grading of CaP and RCC, or confirmation of the specimen as benign (non-involved), by the surgical pathologist (WKF). A total of 22 benign prostate, 22 prostate tumor, 4 benign kidney and 5 kidney tumor specimens for which both an initial tissue specimen and a xenograft specimen were available, were selected for characterization by IHC analysis. Standard avidin-biotin complex peroxidase immunohistochemical staining for huCD31 (PECAM-1, Dako Corp., Carpinteria, Calif.) at 1:25 dilution (13.7 ug/ml), msCD31 (PECAM-1, BD Pharmingen, Bedford, Mass.) at 1:25 dilution (20 ug/ml), CD34 (Santa Cruz Biotechnology Inc., Santa Cruz, Calif.) at 1:75 dilution (2.7 ug/ml), von Willebrand's Factor (Factor VIII Related Antigen, BioGenex, Inc., San Ramon, Calif.) at 1:150 dilution, Ki67 (BD Pharmingen, Inc., San Diego, Calif.) at 1:50 dilution (10 ug/ml), and high-molecular weight cytokeratin (HMW-CK, Enzo Diagnostics, Farmindale, N.Y.) at 1:50 dilution were performed on serial sections. Following antigen retrieval with Citra Buffer (Bio-Genex) or Proteinase K (10 ug/ml in Tris/EDTA buffer), endogenous reactivity for peroxidase and avidin-biotin were blocked prior to primary antibody incubation according to the manufacturer's protocol (Vector Laboratories, Inc., Burlingame, Calif.). Biotinylated secondary antibodies that had been adsorbed against serum of the host animal (Vector Laboratories) were used to visualize specific markers with DAB, Vector Blue, and Vector Red chromogens according to the manufacturer's protocol (Vector Laboratories). Mayer's Hematoxylin or Methyl Green (Sigma, St. Louis, Mo.) was used as nuclear counter-stains. Sections of normal mouse prostate, mouse kidney and human benign prostatic hyperplasia (BPH) were included in all staining procedures as internal controls, with omission of primary antibody serving as the negative staining control.

Image Analysis

Digital images of histochemically and immunohistochemically stained sections were collected using a Kontron ProgRes 3012 camera (TriPath Imaging, Inc., Burlington, N.C.) mounted on an Axioskop microscope (Carl Zeiss, Inc., Thornwood, N.Y.) at 100× magnification, at a resolution of 3072×2320 pixels. Image analysis for manual counts of objects was performed using ImageJ software (Research Services Branch, National Institute of Mental Health, Bethesda, Md.). Where possible, three (3) 100× fields (0.5 mm$^2$) were analyzed to determine the average number of vessels per field (Mean Vessel Density, MVD) and the average number of vessels with at least one proliferating endothelial cell per field (Proliferative Mean Vessel Density, PMVD). The Mean Vessel Area (MVA) and the Mean Vessel Perimeter (MVP) were determined using Optimas 6 image analysis software (MediaCybernetics, Inc., Carlsbad, Calif.).

Statistical Analysis

Descriptive statistics, students paired, unpaired t-tests, and data correlation were performed with Microsoft Excel 2000 (Microsoft Corp., Redmond, Wash.) or Prism 3 (GraphPad Software, Inc., San Diego, Calif.) using a 95% confidence interval. Average MVD, PMVD, MVA, and MVP means were graphed ±SEM.

Establishment of Primary Human Xenografts

Xenografts were established from primary human tissue specimens (44 prostatectomy and 10 nephrectomy) by subcutaneous implantation into athymic nude mice. Briefly, Briefly, the majority of each tissue specimen was cut into wedge-shaped pieces 2-3 mm in length, and 1-2 mm in width at the broadest end, and the wedges were transplanted immediately into male athymic nude mice, three months of age, (Hsd: athymic Nude/Nude, Harlan Sprague-Dawley, Indianapolis, Ind.) that previously had been implanted subcutaneously with 12.5 mg sustained-release testosterone pellets (Innovative Research of America, Sarasota, Fla.) to maintain serum testosterone levels at ~4 ng/ml throughout the study. For implantation of prostate tissue, small (~3 mm) incisions were made in the skin on the right and left flanks of mice anesthetized, tissue wedges to be implanted were dipped in MATRIGEL™, and the coated tissue wedges inserted into the subcutaneous space through a 10 gauge trocar device. Between 3 and 10 wedges from a single patient were implanted along each flank through individual incisions. Incision sites were closed with NEXBAND tissue glue. Xenografts were harvested after 1 month in the host animal and were evaluated for viability at the time of harvest. Viable xenografts were pink-to-red in color, indicating anastomosis to the host vasculature and adequate perfusion. Non-viable xenografts were pale or chalky white, with no visible sign of attachment to the host vasculature, and were determined to be necrotic by histological analysis. The implantation protocol was efficient, with the proportion of surgical specimens that yielded at least one viable xenograft being 92.7% (n=44) for CaP and 97.3% (n=42) for benign prostate, and 100% for malignant and benign kidney surgical specimens (data not shown). Xenografts were established successfully, from both freshly harvested and cryopreserved tissue fragments from nearly 100 successive patients, with per fragment take rates of approximately 60% for freshly harvested tissue and 30% for previously cryopreserved tissue. The histology of the xenografts of CaP and benign prostate generally were consistent with their respective initial tissue specimens, although squamous metaplasia, basal cell hyperplasia, and atrophic glands were observed in the benign prostate xenografts. Xenografts from both RCC and benign kidney specimens contained areas of necrosis, fibrosis and/or fat deposition that were not observed in their corresponding initial tissue specimens.

Vasculature in the Xenografts

We determined the efficiency and distribution of neovascularization or angiogenesis during xenograft establishment in the benign and malignant xenografts compared to the corresponding initial tissue specimens. Vasculature in all initial prostate and renal tissue specimens, and the corresponding xenografts, was identified by immunohistochemical (IHC) analysis with a pan-species antibody against the endothelial cell marker CD31.

In CaP initial tissue specimens and in CaP xenografts the vasculature was found both adjacent to glands and distributed through the stroma (FIG. 1A, B). In contrast, while the vasculature in initial tissue specimens of benign prostate was localized adjacent to glandular structures (FIG. 1C), the vessels in the benign prostate xenografts were disseminated throughout the stroma (FIG. 1D). Areas of necrosis were not observed in the xenografts of prostate tissues, indicating that the efficiency of angiogenesis and the rapidity of re-perfusion of the prostate tissue were sufficient to ensure viability of the entire implant.

The vasculature in the initial tissue specimens and xenografts of RCC and benign kidney tissue was distributed around the glomeruli and was interspersed among the tubules and ducts. (FIG. 1E-H). Compared to glomeruli found in their corresponding initial tissue specimens, glomeruli in the xenografts often were atrophic, circumscribed by scarring, and/or were necrotic (FIG. 1F, H). The consistent observation of areas of necrosis in the xenografts of renal tissues indicated that the efficiency of angiogenesis and the kinetics of re-perfusion of renal tissues were sufficient to support establishment of the xenografts, but inadequate to ensure viability of the entire implant.

Comparison of Vessel Density in Xenografts

Figure 2:
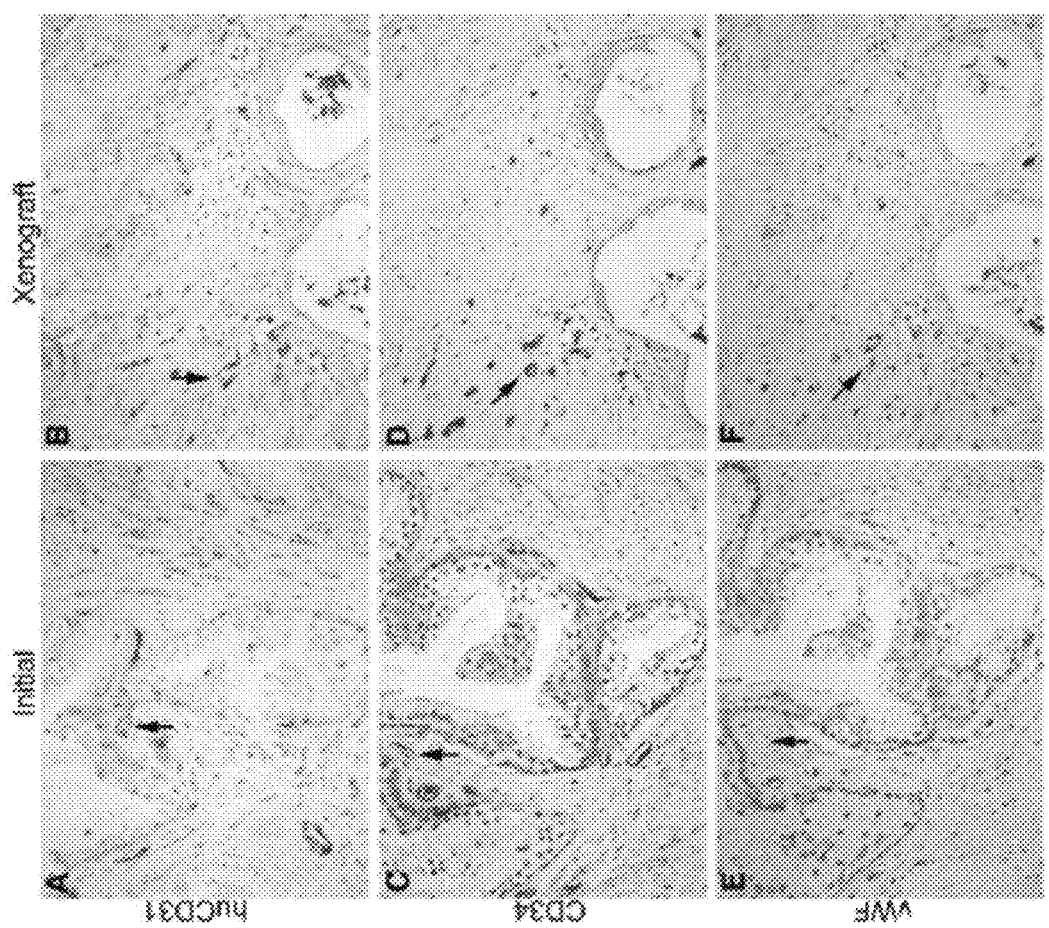
FIG. 2 provides a photographic representation of IHC analysis of expression of endothelial cell biomarkers. Staining of benign human prostate initial tissue and xenograft specimens:Panels A and B, huCD31; Panels C and D, CD34; and Panels E and F, vWF (arrows indicate a single vessel in all three panels). Magnification, ×200.
Figure 3:
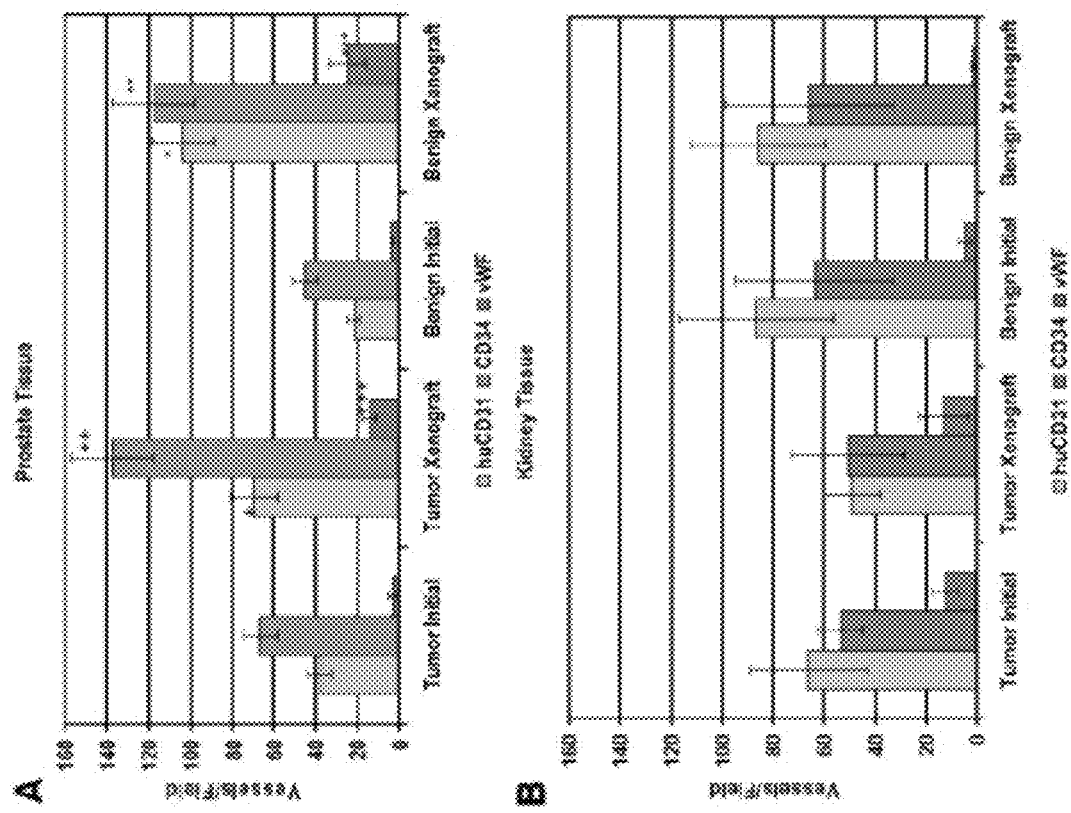
FIG. 3 provides a graphical representation of quantification of prostate and kidney vascular staining with three vascular endothelial cell markers represented graphically as vessels/field by time point and by vascular marker. Initial, initial tissue specimen; Xenograft, tissue established in the host ≥1 month. Panel A, prostate tissue. Tumor: huCD31, n=22 and 14, +, P=0.009; CD34, n=14 and 7, ++, P=0.020; and vWF, n=8 and 7, +++, P=0.007. Benign: huCD31, n=22 and 14, *, P<0.001; , CD34, n=14 and 7, P=0.003; and *, vWF, n=8 and 7, P>0.05. Panel B, RCC and benign kidney: huCD31, CD34, and vWF, n=3-5, P>0.05. Data shown are means; bars, SE.

CD31 (PECAM-1), CD34 (myeloid progenitor cell antigen) and von Willebrand's Factor (vWF, Factor VIII Related Antigen) are markers of endothelial cells that have been utilized to quantitate microvessel density in CaP. As shown in FIG. 2, serial sections of benign initial prostate tissue and corresponding xenograft specimens were stained for CD31 (FIG. 2A, B), CD34 (FIGS. 2C, D), and vWF (FIGS. 2E, F) to establish which marker detected the largest number of vessels in the xenografts. Each of the three markers failed to stain all of the vessels in the tissue specimens or the xenografts; CD34 and CD31 generally stained approximately equal number of vessels, and both stained significantly more vessels than vWF. The vessels positive for each marker in the prostate initial tissue and xenografts were counted in three highly vascular fields (0.5 mm$^2$) per specimen and the results were quantitated as the Mean Vessel Density, MVD (FIG. 3). The MVD in the xenografts from CaP tissue was increased significantly compared to the MVD in the corresponding CaP initial tissue specimens: CD31 MVD increased 1.8-fold in xenografts, CD34 positive vessels increased 2.1 fold and vWF positive vessels increased 4.1-fold (FIG. 3A). Similarly, the MVD measured by these three vessel markers was increased significantly in the benign prostate xenografts compared to the benign prostate initial tissue specimens: CD31 increased 4.8-fold, CD34 staining increased 2.6-fold and vWF staining increased 6.9-fold (FIG. 3A). In contrast, there was no increase in MVD in xenografts established from the more highly vascularized RCC, or from benign renal tissues, compared to their initial tissue specimens (FIG. 3B). CD31 or CD34 stained fewer vessels in the prostate and renal initial tissue specimens, however they stained approximately equal numbers in the prostate and xenografts. Because CD31 is proposed to be more specific for angiogenic endothelial cells than CD34 CD31 was utilized for quantitation of vasculature in subsequent studies.

Species Specific Vascular Labeling

Figure 4:
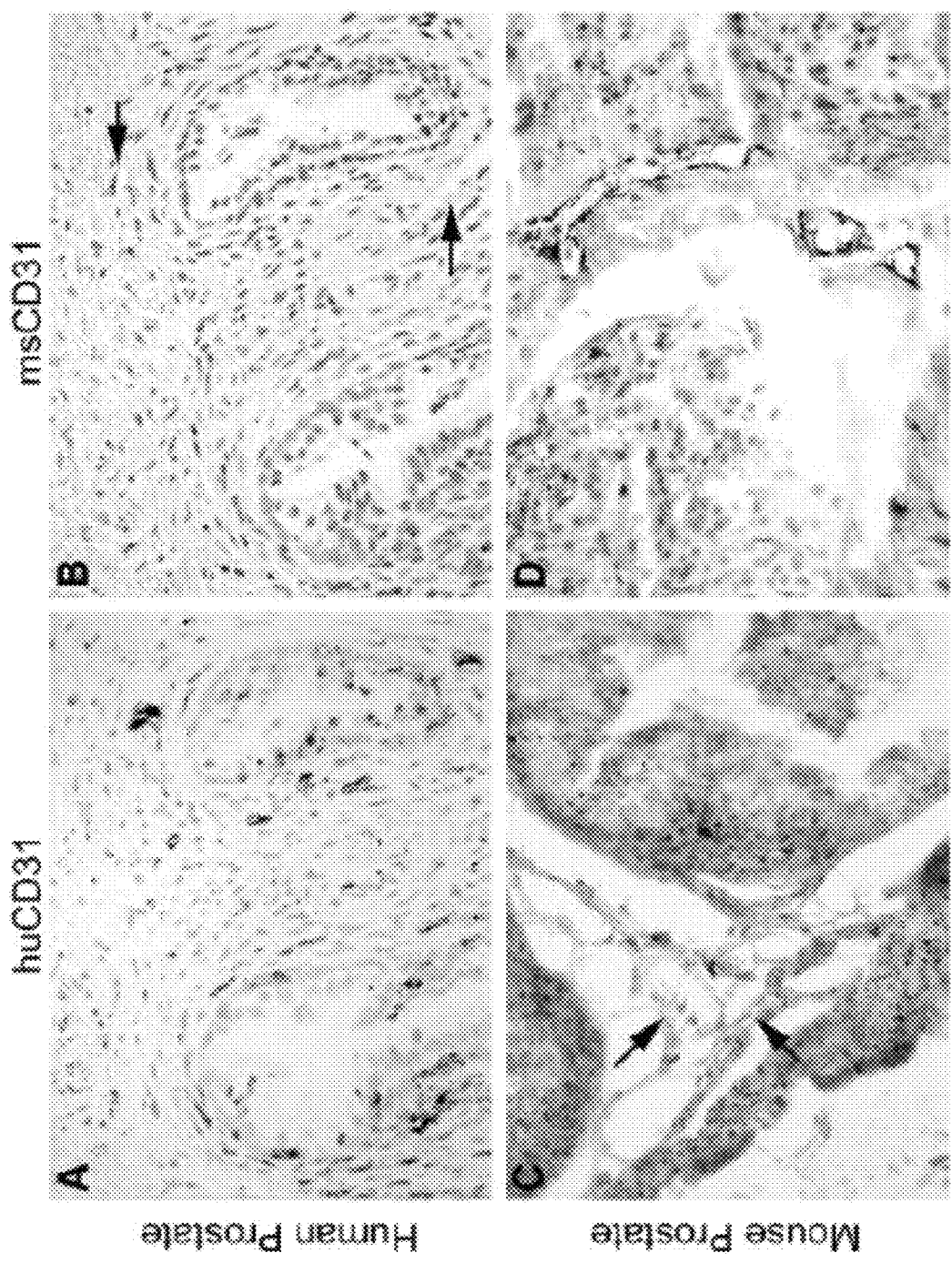
FIG. 4 provides a photographic representation of species specificity of immunological probes for human and mouse vascular markers. Staining of benign human prostate initial tissue with huCD31-specific antibody (Panel A) and for msCD31-specific antibody (Panel B; arrows indicate unstained vessels). Staining of benign mouse prostate tissue with huCD31-specific antibody (Panel C; arrows indicate unstained vessels) and for msCD31-specific antibody (Panel D). Magnification, ×200.

The studies presented in FIG. 3 utilized anti-human CD31 to identify the vasculature in the CaP and benign prostate xenografts and indicated that the angiogenesis apparent in the prostate xenografts was by human vessels in the human xenograft, not by host mouse vessels. Consequently, the origin of the vasculature in the xenografts was analyzed using species-specific anti-CD31 antibodies. The species specificity of a rat monoclonal antibody specific for mouse CD31 (msCD31) and a mouse monoclonal antibody specific for human CD31 (huCD31) was verified by immunohistochemical analysis of human and mouse control tissues (FIG. 4). The huCD31 antibody labeled endothelial cells in human benign prostatic hyperplasia (BPH) specimens (FIG. 4A) but did not label endothelial cells in mouse prostate tissue (FIG. 4C). In contrast, the msCD31 antibody labeled mouse endothelial cells in mouse prostate tissue (FIG. 4D) but showed no vascular reactivity in human BPH tissue (FIG. 4B).

The species of origin of the vasculature in the prostate and kidney xenografts was determined by IHC analysis of serial sections with huCD31 and msCD31 (FIGS. 5C-F). The number of vessels positive for each of the species-specific CD31 antibodies were counted in three highly vascular fields (0.5 mm$^2$) per section and averaged. The percentage of human vessels in the xenografts at one month after implantation was calculated as the number of huCD31 positive vessels divided by the sum of the huCD31 positive and msCD31 positive vessels per field. The percentage of human vessels in the prostate xenografts, in spite of the significant increase in the number of vessels per field relative to the initial tissue, was 79.3±4.8% (n=30). The percentage of human vessels in kidney xenografts was 90.4±1.8% (n=10), although there was no significant increase in MVD. In xenografts of either prostate or renal tissue, the vessels that stained with the mouse specific CD31 (msCD31) were localized mainly in a compressed connective tissue layer at the periphery of the xenografts that presumably was host tissue (not shown), however, vessels of mouse origin occasionally penetrated into the xenografts suggesting limited angiogenesis by host vasculature.

Quantitation of Human Vessel Density and Endothelial Cell Proliferation

Figure 5:
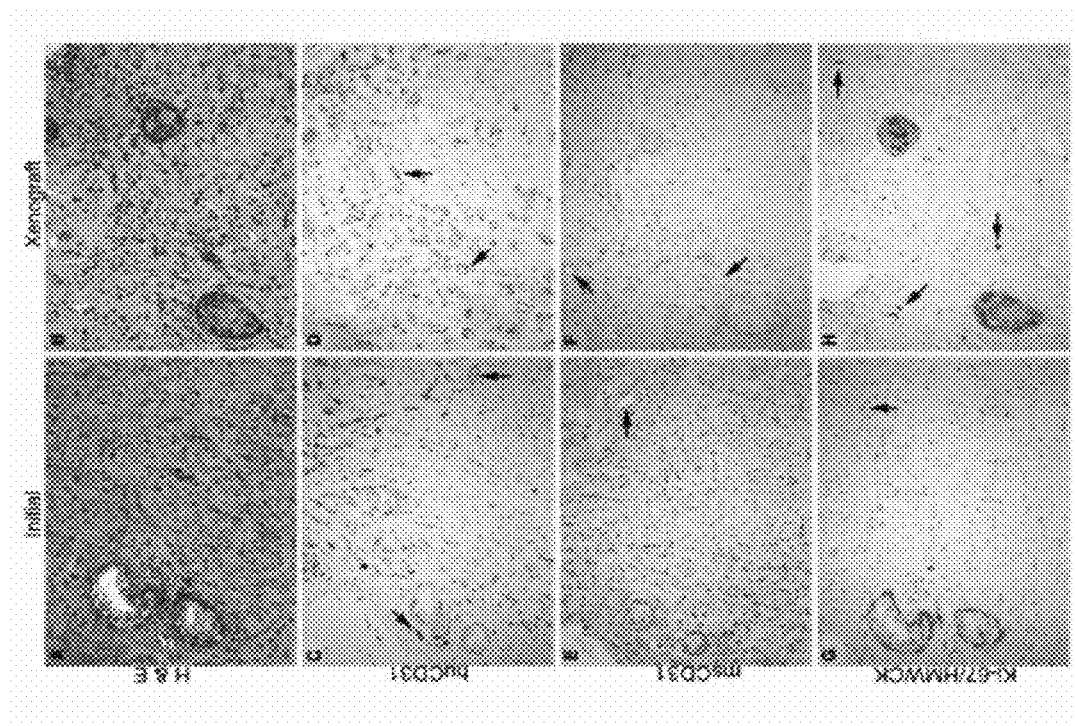
FIG. 5 provides a photographic representation of analysis of species of origin and proliferation of endothelial cells of benign prostate initial tissue and xenograft specimens. Panels A and B, benign prostate tissue architecture (H&E). Panels C and D, human vessel staining (arrows indicate human vessels; huCD31). Panels E and F, mouse vessel staining (arrows indicate unstained vessels; msCD31). Panels G and H, cellular proliferation marked by nuclear staining by Ki-67 (black; arrows indicate proliferating vessels). Basal cells of prostate glands visualized by staining for high-molecular weight cytokeratin (HMWCK; 34βE12 antibody). Magnification, ×100.

The magnitude of the angiogenic response associated with establishment of the xenografts was compared to the vascularization of the initial tissue by IHC analysis of serial sections of initial tissue specimens and xenografts of benign and carcinomatous prostate and kidney specimens with huCD31, msCD31, and Ki-67 (proliferation marker) plus high molecular weight cytokeratin (34βE12, a basal cell marker) (FIG. 5). Normal prostate glandular architecture, characterized by epithelial cell lined glands with adjacent stroma, was observed in the initial benign tissue specimens (FIG. 5A) and in benign prostate xenografts (FIG. 5B). The presence of a basal cell layer that stained positive for 34βE12 surrounding the glandular structures confirmed the specimens were benign prostate. A low number of huCD31 positive vessels (dark brown) were observed in the initial tissue specimen (FIG. 5C). In contrast, a large number of small-to-medium caliber huCD31 positive vessels were dispersed throughout the xenografts (FIG. 5D), and represented a 5-fold increase in MVD compared to the initial prostate tissue specimen (FIG. 6B). MsCD31 positive vessels generally were absent from the interior of xenograft specimens (FIG. 5E, F), consistent with the peripheral location of mouse vessels described above. In initial benign tissue specimens, essentially no vessels were observed with Ki-67 positive endothelial cells (FIG. 5G). However, the proliferative mean vessel density, PMVD, of the benign prostate xenografts increased 8-fold compared to their initial tissue specimens, with endothelial cells with Ki-67 positive nuclei observed in vessels near glandular structures as well as in vessels dispersed within the stroma (FIG. 5H). CaP xenografts also demonstrated significant increases in MVD (2 fold), and PMVD (5 fold), compared to the initial CaP specimens (FIG. 6A). In contrast, there was a decrease, though not statistically significant, in MVD in the RCC xenografts compared to the initial RCC tissue specimens, while the PMVD remained unchanged (FIG. 6A). The MVD and PMVD were unchanged in the benign kidney xenografts compared to the initial tissue specimens (FIG. 6B).

Quantitation of Vessel Dimensions

Figure 7:
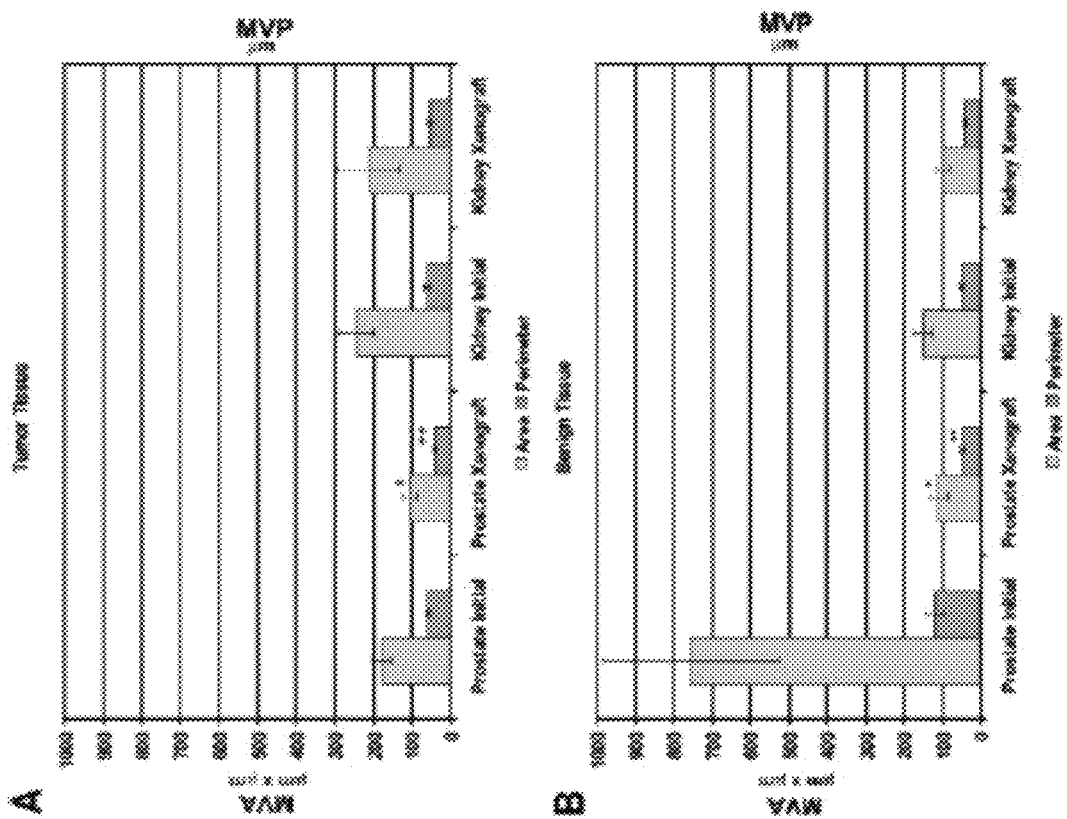
FIG. 7 provides a graphical representation of quantification of prostate and kidney vascular dimensions represented as microvessel area (MVA) and microvessel perimeter (MVP) by growth condition, initial tissue and xenograft. A, tumor tissue: prostate (MVA, n=6, +, P=0.048; MVP, n=6, ++, P=0.007); kidney (MVA and MVP, n=5, P>0.05). B, benign tissue: prostate (MVA and MVP, =5, *, P=0.01); kidney (MVA and MVP, n=4, P>0.05). Data shown are means; bars, SE.

CD34 staining of the vasculature in xenografts presented in FIG. 1 indicated that the size of the angiogenic vessels in the xenografts of CaP and benign prostate were substantially smaller than the vessels in initial prostate tissue specimens (FIG. 1A-D). In contrast, there appeared to be little difference in vessel size between the initial renal tissue specimens and the corresponding benign and RCC xenografts (FIG. 1E-H). Consequently, vascular dimensions in huCD31 stained serial sections of benign prostate, CaP, benign kidney and RCC initial tissue specimens and xenografts were characterized by measurement of the area and perimeter of all huCD31-stained vessels in 3 microscopic fields (0.5 mm$^2$). The mean vessel area (MVA) and mean vessel perimeter (MVP) were reduced significantly (1.7-fold) in CaP xenografts compared to the corresponding initial tissue specimens (FIG. 7A). Similarly, the MVA was reduced 7-fold in benign prostate xenografts compared to the initial tissue specimens, and the MVP showed a 2.5-fold decrease (FIG. 7B). In contrast, the RCC and benign kidney xenografts showed no significant difference in MVA and MVP compared to the corresponding initial tissue specimens (FIG. 7A, B).

Example 2

This Example demonstrates that androgen deprivation induces several rapid but transient changes in the prostatic microenvironment.

Androgen deprivation therapy was initiated at one month post-implantation of xenografts by castration of the host animal comprising human xenografts obtained as set forth in Example 1, and removal of the testosterone pellet. Control hosts were subjected to mock castration by making and closing a scrotal incision without orchiectomy and without removal of the testosterone pellet. Host animals were euthanized and xenograft tissues collected immediately after androgen deprivation/mock castration (Day 0), or on Days 1, 2, 4, 7, 14 or 28 following androgen deprivation/mock castration. Harvested xenografts were fixed in 10% formalin for a minimum of 24 hrs, after which the fixed tissues were paraffin-embedded. Paraffin blocks were sectioned (5 μm) onto slides.

Perfusion of Host Vasculature

In preparation for immunofluorescence staining and confocal microscopy, the vasculature of human prostate primary xenografts was cleared of red blood cells and fixed by perfusion of the host mouse vasculature with 10% paraformaldehyde in phosphate buffered saline (PBS) via cardiac puncture. Perfusion was performed with the animals under anesthesia induced by intraperitoneal injection of AVERTIN (SIGMA) at a concentration of 0.62-0.74 ml/25-30 g or 2500-500 mg/kg, and the animals exsanguinated during the perfusion. Briefly, animals were anesthetized and checked for lack of pain response, the chest cavity opened, and a 5 ml preparation of para-formaldehyde/PBS injected into the left ventricle with the vena cava cannulated for drainage. Following vascular fixation, the animals were perfused with an additional 10-15 ml PBS, the subcutaneous xenografts harvested, the xenografts frozen in Tissue Freezing Medium (TFM) on a cryotome chuck and the specimens stored at −80 degrees C.

Immunohistochemical Analysis

A histological specimen was prepared from each IT specimen harvested before implantation, and from each corresponding xenograft specimen, and the sections stained with AMACR (racemase) to assess the presence of CaP. Complete specimen sets from eight patients that included an IT specimen and all Short Time Point Post-Castration (STP-PCX) specimens were characterized by IHC analysis for the pattern of expression of angiogenesis-related proteins and steroid receptors.

Tissue sections were de-paraffinized, hydrated through graded washes with ethanol and de-ionized water, and equilibrated in automation buffer. Antigen retrieval was performed on the histologic sections by steaming or boiling the slides in 10 mM citric acid buffer (pH 6), or by trypsin digestion (0.5 mg/ml Trypsin, in 34 mM CaCl/50 mM Tris Buffered Saline with 5 mM EDTA, pH 8). Endogenous peroxidase activity and background avidin-biotin reactivity were blocked prior to the quenching of nonspecific antibody binding. Sections were incubated with antigen-specific antibodies at optimized dilutions in common antibody diluent for 30 minutes at 37° C., followed by incubation for 20 minutes at 37° C. with a biotinylated secondary antibody matched to the host species of the primary antibodies. Immunoreactive targets were visualized using peroxidase chromagen kits. Slides were counterstained with Methyl Green to identify nuclei, dehydrated with ethanol, and mounted. Sections of human benign prostatic hyperplasia (BPH) were included in all staining procedures as positive controls, and omission of primary antibody served as the negative immunostaining control.

Image Analysis

Digital images of immunohistochemically stained sections were collected using a Kontron ProgRes 3012 camera (TriPath Imaging, Inc., Burlington, N.C.) mounted on an Axioskop microscope (CARL ZEISS, Inc., Thornwood, N.Y.) at 100×, 200×, 400× and 630× magnification, depending on the intended use of the images, at a resolution of 1996×1450 pixels. Image analysis for manual counts of objects was performed using the ImageJ software with the Cell Counter Plug-In (Research Services Branch, National Institute of Mental Health, Bethesda, Md.). Where possible, three (3) 100× (0.480 mm$^2$), 200× (0.120 mm$^2$) or 400× (0.030 mm$^2$) fields were collected, and analyzed. For manual scoring of histological specimens, the investigator was blinded to the origin of the specimen.

Dual Fluorescence Whole Mount Immunohistochemistry

To evaluate the histology of the frozen perfused xenografts prior to whole mount immunohistochemistry, the xenografts were sectioned on a cryostat, using a 5 μm thick setting, until the encasing mouse tissue was cut through. A 5 μm section containing xenograft tissue with the circumscribing host mouse cuff was stained with Hematoxylin and Eosin Y and examined for histological characterization. The remainder of the frozen xenograft whole mounts, (approximately 3 mm×3 mm×3 mm), were placed in 15 ml conical tubes in PBS, thawed, washed with 1× Automation Buffer to remove the TFM, the tissue permeabilized by incubation in 1% Triton-X/PBS, and non-specific immuno-reactivity blocked. Dual IHC staining was performed by incubation of the xenografts that contained antibodies specific for human CD31 (0.003 mg/mL) and CD34 (0.25 mg/mL), and for androgen receptor (AR; 0.003 mg/ml), for 30 Minutes at 37 degrees C. After incubation with the primary antibodies, the xenografts were rinsed with Automation Buffer, incubated in a solution of Alexa Fluor 594-labeled goat anti-rabbit IgG (1:1,000 dilution) (INVITROGEN, CORP.—MOLECULARPROBES, Carlsbad, Calif.) and Alexa Fluor 488-labeled donkey anti-mouse IgG (1:1,000 dilution) in Power Block, for 30 minutes at 37 degrees C., and rinsed with Automation Buffer. After incubation with the primary and secondary antibodies, the tissue was dehydrated by serial incubation in a graded series of alcohol solutions (50%, 70%, 95% and 95% ethanol) for 3 minutes each at room temperature, and the dehydration completed by incubation in three changes of 100% ethanol for 30 minutes at room temperature. In preparation for Confocal Laser Scanning Microscopy (CLSM), the fluorescently stained xenografts were cleared by incubation in Methyl Salicylate (synthetic oil of wintergreen) overnight at room temperature, the oil of wintergreen removed, and fresh oil of wintergreen added for an additional 4 hour incubation immediately prior to CLSM analysis.

Confocal Microscopy Image Collection and Analysis

Immunostained and optically cleared xenografts were placed on chamber slide-bottomed Petri dishes, the tissue covered with Methyl Salicylate and the xenograft imaged on a Zeiss LSM 5 Pascal Confocal Microscope system (CARL ZEISS, Oberkoken, Germany) using a 40× Apochromat, 1.3 NA Oil objective lens. Z-slices were collected at 1 μm intervals to a depth of approximately 125 μm. Z-Projection 3D images were generated from the serial optical sections for FITC Fluorescence (CD31 and CD34), Rhodamine Fluorescence (AR), and FITC plus Rhodamine Fluorescence (co-localization). The images were analyzed for co-localization of fluorescent probes using both the Zeiss LSM software (Release 3.2) and ImagePro Plus (Release 5.0) (Media Cybernetics, Inc., Silver Springs, Md.) to generate the Pearson's Correlation Coefficient (Rr), Overlap Coefficient according to Manders (R), Overlap Coefficients (k1 & k2) and Colocalization Coefficients (m1 & m2).

Analysis of Expression of Angiogenic Factors

Figure 10:
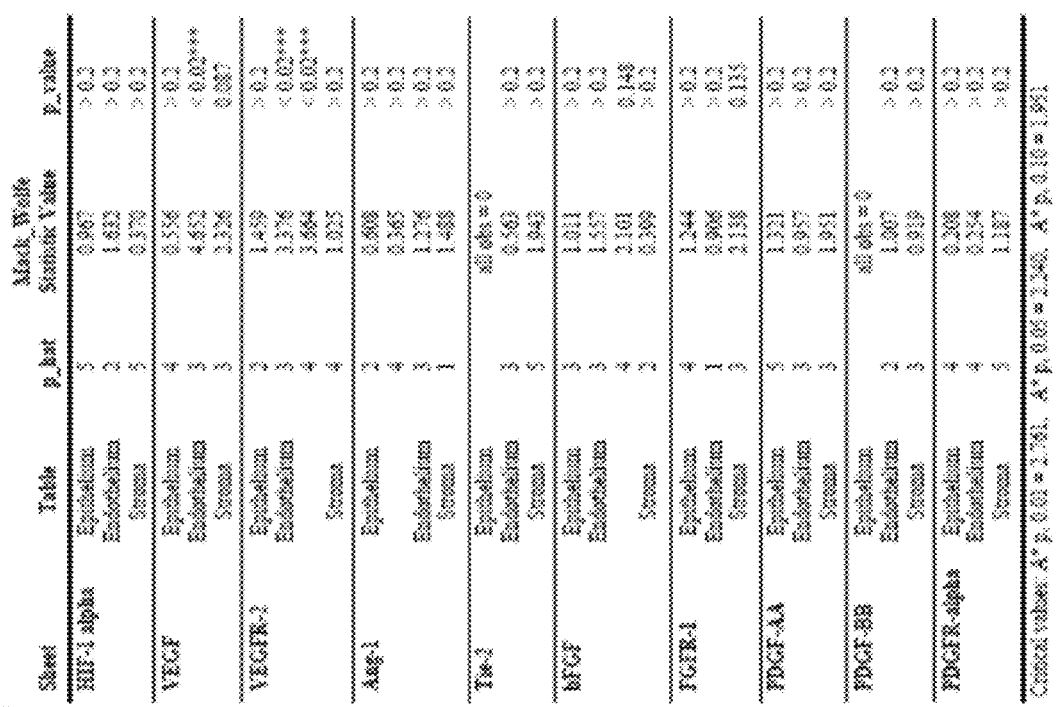
FIG. 10 provides a tabular summary of a statistical analysis of immunohistochemical staining indicating the presence of specific proteins that are associated with angiogenesis. The primary observation that can be drawn from these data is that that VEGF and bFGF are the only pro-angiogenic factors whose expression is dramatically increased in the short time period after castration.

Short time point, post-castration (STP-PCX) human prostate primary xenograft specimens were stained by IHC for expression of selected angiogenesis-related factors (VEGF, bFGF, PDGF-AA and PDGF-BB), their cognate receptors (VEGFR-2, FGFR-1, PDGFR-α, and Tie-2), Hypoxia Inducible Factor-1 alpha (HIF-1α), estrogen receptor-alpha (ER-α), estrogen receptor-beta (ER-β) and androgen receptor (AR), and the levels of expression were evaluated manually. The results are presented in FIG. 10. Expression of the individual proteins in the epithelial, endothelial, and stromal compartments were scored independently. The scoring system was based upon the intensity of staining: 0 (no stain), 1 (weak stain), 2 (moderate stain), and 3 (strong stain), with the assigned score representing the level of expression in the majority of the cells in each compartment. Levels of expression in each prostatic compartment were scored at each time point post-androgen deprivation for multiple microscopic fields from each xenograft for each patient; and the scores averaged across all samples from all patients at each time point. Two investigators, blinded to the origin of the specimen, scored each slide independently and the scores were averaged for a composite staining intensity. Inter-observer scoring of the levels of protein expression demonstrated significant concordance (r=0.90).

Statistical Analysis

Data sets were prepared for statistical analyses by categorizing blank values as: Missing Completely At Random (MCAR), Missing at Random (MAR) or Not Missing At Random (NMAR). The source of blanks in data sets were attributed to two sources: A) time points where the mouse host died prior to harvest of the xenograft, and B) time points where the xenograft was harvested but the sample was either mostly adipose tissue or could not be processed for IHC. Condition A blanks were treated as MCAR and the blank filled using the mean imputation method of supplying a single estimator, the mean value for that time point without the missing data point. Condition B blanks occurred as multiple sequential blanks, rather than random individual blanks, and led to the removal of two patient sample sets. The occurrence of sequential blanks usually resulted from the scoring of specimens as being predominately adipose tissue.

Temporal analyses of the effect of androgen deprivation on xenografts from a single patient were enabled by fragmentation of the surgical specimen, and implanting the multiple tissue pieces into a cohort of animals. This approach allowed analysis by patient, by time point, and by condition, and the 5% alpha value applied to the paired student t-tests or Wilcoxon Signed Rank tests was divided by the total possible pairings to take a family wise effect approach to the statistical analysis. However, specimens for analysis of sequential time points for a single patient were maintained in separate mouse hosts, suggesting a pair wise application of the 5% alpha for each test. Consequently, significant pair wise P values, as well as significant family wise P values, are indicated in the results. Additionally, descriptive statistical analysis, including median, mean, count, standard deviation and normality testing (Shapiro-Wilk and Kolmogorov-Smirnov with Dallal-Wilkinson-Lilliefor P value) were calculated to confirm or reject the assumption of normality for mean comparison tests (students t-test or Wilcoxon Signed Rank test). Both power analysis and sample size estimation were performed in the design of this study.

Analyses of data sets from castrate hosts in studies with 5-time points/patient (Day 0, and Days 1, 2, 4 and 7 after castration) utilized a paired two-tailed Student T-test or a Wilcoxon Signed Rank test (95% Confidence) between the ten possible comparison pairs (Day 0 to Day 1, Day 0 to Day 2, Day 0 to Day 4, Day 0 to Day 7, Day 1 to Day 2, Day 1 to Day 4, Day 1 to Day 7, Day 2 to Day 4, Day 2 to Day 7, and Day 4 to Day 7). A 5% alpha was applied to each pair wise test and a 0.5% alpha was applied to each family wise test.

Analysis of the expression of steroid receptors, hypoxia inducible factor-1α and angiogenesis-related factors based upon the intensity scores was performed using a Mack-Wolfe Unimodal Umbrella Test with Unknown Peak, adapted for Two-Sided analysis of p-values (463). The described critical values were used to interpret p-values between 0.02 and 0.2.

Descriptive statistics, normality testing, students paired t-tests, Signed Rank tests, and data correlations were performed using Prism 4 (GraphPad Software, Inc., San Diego, Calif.). Power and Sample Size analysis was performed using StatMate 2 (GraphPad). Standard Error of the Mean (SEM) calculations were performed with Microsoft Excel 2003 (Microsoft Corp., Redmond, Wash.). All data, with the exception of the staining intensity scores, were graphed ±SEM.

The data obtained from employing the foregoing materials and methods in this Example are as follows.

Effect of Androgen Deprivation on the Vasculature in Human Prostate Xenografts.

The response of the vascular endothelium, glandular epithelium, and stromal compartments of the prostate xenografts to androgen deprivation was evaluated by immunohistochemical analysis using Ki-67 to identify proliferatively active cells, and activated Caspase-3 to identify apoptotic cells, in each of the three cellular compartments in xenografts harvested immediately after androgen deprivation/mock castration, and after one, two, four and seven days of androgen deprivation. Co-staining with a cocktail of antibodies specific for human-CD31 and CD34 was utilized to identify apoptosis and proliferation specifically in the vascular endothelial cells in the xenograft tissue (FIG. 8A). Dual-IHC staining of endothelial cell and proliferation markers in xenografts harvested at Day 0, prior to androgen deprivation, and at thirty days post-androgen deprivation, allowed characterization of the effect of androgen deprivation on mean vessel density (MVD) and vessel proliferation index (VPI, the percentage of vessels with at least one proliferative endothelial cell) in the human prostate xenografts. There was no significant difference in MVD (P=0.6557, Paired t-Test; P=0.3394, Wilcoxon) between xenografts harvested on Day 0 and on Day 30 post-androgen deprivation. In addition, there was no difference in mean vessel perimeter (MVP) or mean vessel area (MVA) between the pre-androgen deprivation time point and Day 30 post-androgen deprivation (data not shown). However, there was a significant difference in the VPI (P=0.0129, Paired t-Test; P=0.0098, Wilcoxon) between xenografts harvested on Day 0 and Day 30 post-androgen deprivation. These data suggest that after 30 days of androgen deprivation the number of vessels resulting from revascularization had recovered largely to pre-androgen deprivation levels, although the vessels were smaller. This suggests the vascular damage induced by androgen deprivation is transient.

Acute Effect of Androgen Deprivation on the Vasculature of Human Prostate Xenografts.

The effect of androgen deprivation on the prostatic vasculature observed at Day 30 after androgen deprivation could represent the maximal level of vascular injury, reflecting damage that progressively increased with time, or conversely, could represent a partial recovery after a maximal level of injury incurred at an earlier time point after androgen deprivation. The acute effect (i.e., over the first 2-4 days post-castration) of androgen deprivation on prostate vasculature, therefore, was characterized by evaluation of primary xenografts of human prostate tissue harvested from hosts that were mock-castrated, or castrated and the supplemental testosterone pellets removed, at short time points after androgen deprivation. Xenografts were harvested on the day of castration (Day 0) within 2-4 hours after the surgery, or on Days 1, 2, 4 or 7 after surgery. Immunohistochemical analysis of serial histological specimens was performed by quantitation of Mean Vessel Density (MVD), Vessel Proliferation Index (VPI) and Vessel Apoptotic Index (VAI). Vascular endothelial cell nuclei, and endothelial cell nuclei stained for activated Caspase-3 or Ki-67, were quantified manually in digital microscopic images. Specimens from each of eight patients were engrafted to a sufficient number of hosts to allow harvest at all of the five time points following androgen deprivation (Days 0, 1, 2, 4 and 7). Following IHC and histological quantitation, statistical analyses of data for MVD, VAI and VPI for family wise effect ($\alpha=0.005$) and pair wise effect ($\alpha=0.05$) were performed using the Paired t-Test and Wilcoxon Signed Rank Test: graphs are annotated to denote pairs with pair/family wise significance (FIGS. 8B-8C, respectively). Pair wise analysis of MVD failed to demonstrate statistical significance; however, the data demonstrated a decrease to a nadir between Days 1 to 2 after androgen deprivation, and a rebound by Day 7, returning nearly to the pre-castration MVD (FIG. 8B). The VAI demonstrated an inverse pattern to the changes observed in MVD, with a nearly two-fold increase in VAI between Day 0 to Day 2, followed by significant decreases from Day 2 to Day 4 and Day 2 to Day 7 (FIG. 8C). Finally, a decrease in the VPI was observed between Days 0/1 and Day 2, Day 4 and Day 7 (FIG. 8D). The effects on testosterone levels is presented in FIG. 8E. These studies indicate that the most significant effects of androgen deprivation upon vascular integrity in the prostate xenografts occurred acutely after androgen deprivation, and that by 7 days after androgen deprivation there was some recovery, which may continue for as long as 30 days.

Acute Effect of Castration on the Epitheliem and Stroma of Human Prostate Xenografts.

Figure 9:
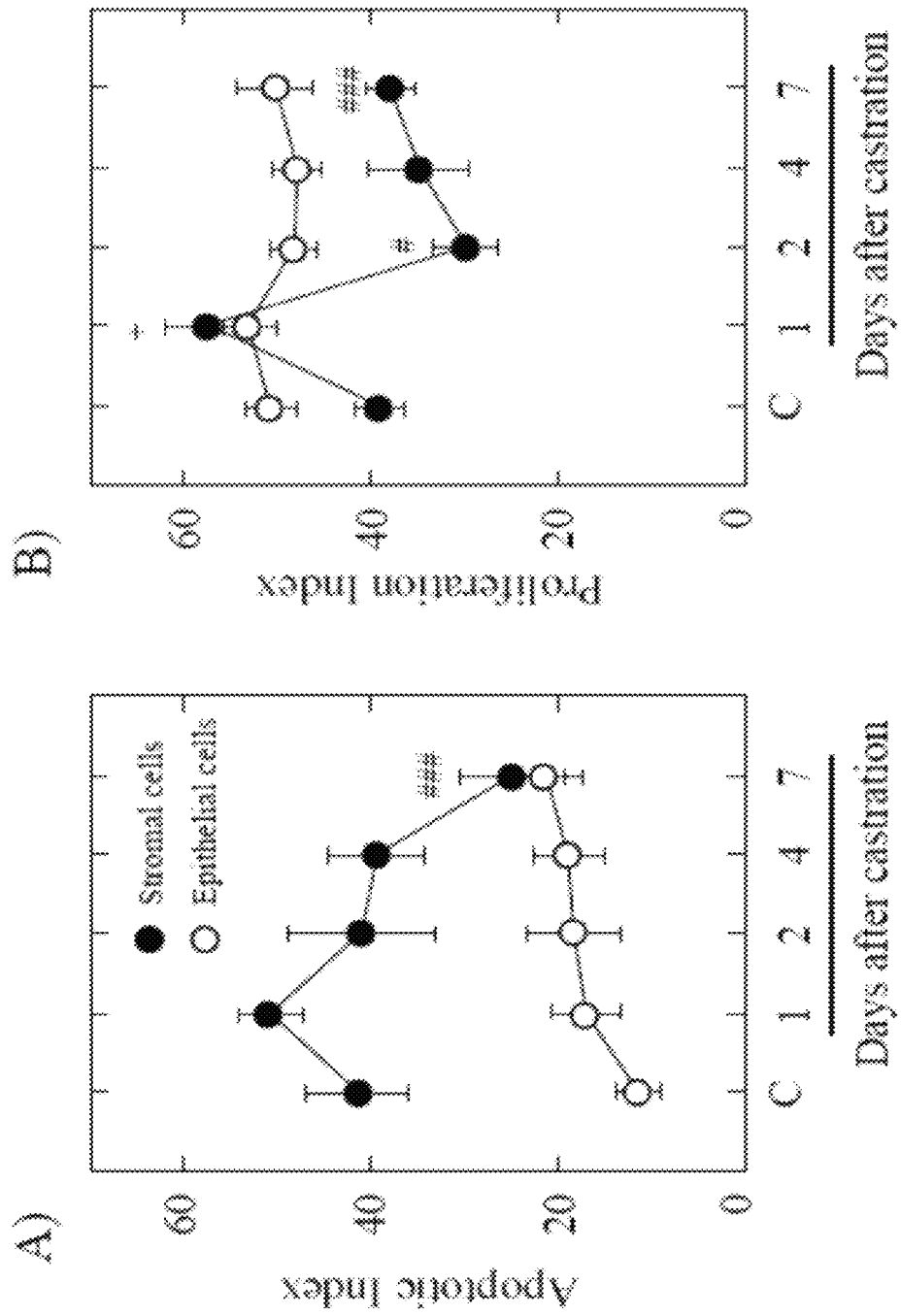
FIG. 9 in panels A and B provides a graphical representation of changes in apoptotic and proliferation indices, respectively, for stromal cells and epithelial cells in human prostate xenografts over time after castration.

The effect of androgen deprivation on the glandular epithelial and stromal compartments was determined at short time points after androgen deprivation to correlate the temporal nature of the responses of these compartments relative to the vascular endothelial cell compartment. Immunohistochemical analysis of serial sections to those characterized for endothelial markers were performed for quantitation of epithelial apoptotic index (EpAI), epithelial proliferation index (EpPI), stromal apoptotic index (StAI) and stromal proliferation index (StPI). The data indicates a progressive increase in epithelial cell apoptosis from Day 0 to Day 7, with no obvious change in proliferation index evident over the same period (FIG. 9, panel A). Consequently, the apoptotic effect of androgen deprivation on epithelial cells may peak later than seven days after androgen deprivation. In contrast, both the StAI and StPI increased acutely from Day 0 to Day 1 in response to androgen deprivation, and decreased significantly between Day 1 to Day 7 (FIG. 9, panel B). As observed with the acute effect of androgen deprivation on the vascular endothelial compartment, the data for the glandular epithelial and stromal compartments indicates that important effects of androgen deprivation on the prostate tissue microenvironment occurred acutely, and that prostate tissue homeostasis was re-established by Day 7 in the absence of androgen. In particular, stromal cells, of which only a small fraction express AR and are expected to by sensitive to androgen stimulation, demonstrate a rapid induction of cell death in a small fraction of cells in response to androgen deprivation. Importantly, apoptosis in the epithelial compartment gradually increases and apparently peaks after Day 7. This is of significance since it is commonly believed that the epithelial cells are the most androgen sensitive cells in the prostate. In panel B, proliferation in the stromal cells of prostate falls over the first 2 days, but recovers by Day 7. However, there is essentially no change in proliferation in epithelial cells, as might be expected from FIG. 8. It should be noted that the endothelial cells in FIG. 8 appear far more sensitive and respond much faster than the epithelial cells (i.e., the cells that resemble cancer cells), and that the endothelial cells recover rapidly in the absence of androgen that, before castration, had regulated their growth and survival, suggesting the unmasking/induction of new therapeutic targets.

Androgen Receptor Expression in Prostate Vascular Endothelial Cells

Figure 12:
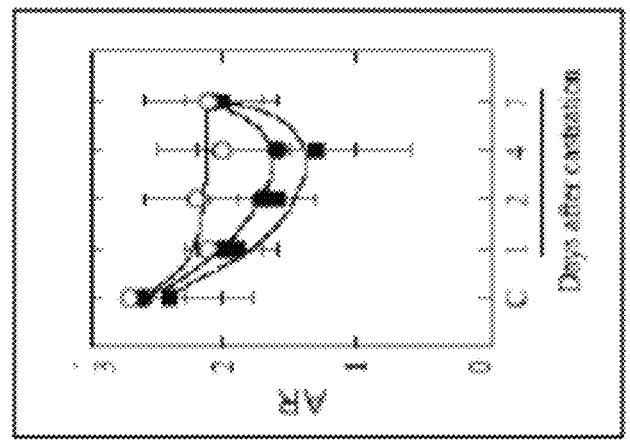
FIG. 12 provides a tabular and graphical summary of the effects of castration on androgen receptor (AR). In the absence of androgen, it would be expected that AR would be significantly depleted. While this effect is observed, AR unexpectedly reappears by Day 7, being stabilized and activated by some unknown mechanism.

The rapid induction of endothelial cell apoptosis, and the associated reduction of MVD indicated by reduced staining with anti-human CD31/CD34, suggested the potential of a direct effect of androgen deprivation on survival of prostate endothelial cells. A dual immunohistochemical staining protocol using the combination of human specific CD31 and CD34 antibodies, and AR-specific antibodies, was developed to determine if human prostate endothelial cells expressed AR. In xenografts harvested from intact (non-androgen deprived) hosts, AR was identified by dual IHC studies as sequestered in the nuclei of endothelial, epithelial and stromal cells (FIG. 12). Expression of AR by the vascular endothelial cells was verified subsequently by co-localization of AR and CD31/CD34 by dual immunofluorescence assay in whole xenografts harvested from intact hosts that were perfused in situ with antibodies specific for AR and CD31/34. Endothelial cell membranes were labeled with CD31/34 and AR label was observed localized in the cytoplasm. Confocal laser scanning microscopic (CLSM) analysis for co-localization of stains in the dual stained, and Methyl Salicylate cleared, xenografts demonstrated a very high degree of cellular colocalization of CD31/34 and AR (Pearson's correlation, Rr=0.967815; Overlap coefficient, R=0.985040; Overlap coefficient, k1=0.796873; Overlap coefficient, k2=1.217639; Co-localization (ch2>0), m1=0.997502; Co-localization (ch1>0), m2=0.997493). Colocalization and Overlap CLSM analysis of control tissues stained for either the endothelial cell markers or for AR demonstrated no co-localization as evidenced by co-incidence of the individual fluorescence signals.

Alteration in Protein Expression in the Prostate Cellular Compartments in Response to Androgen Deprivation.

Figure 11:
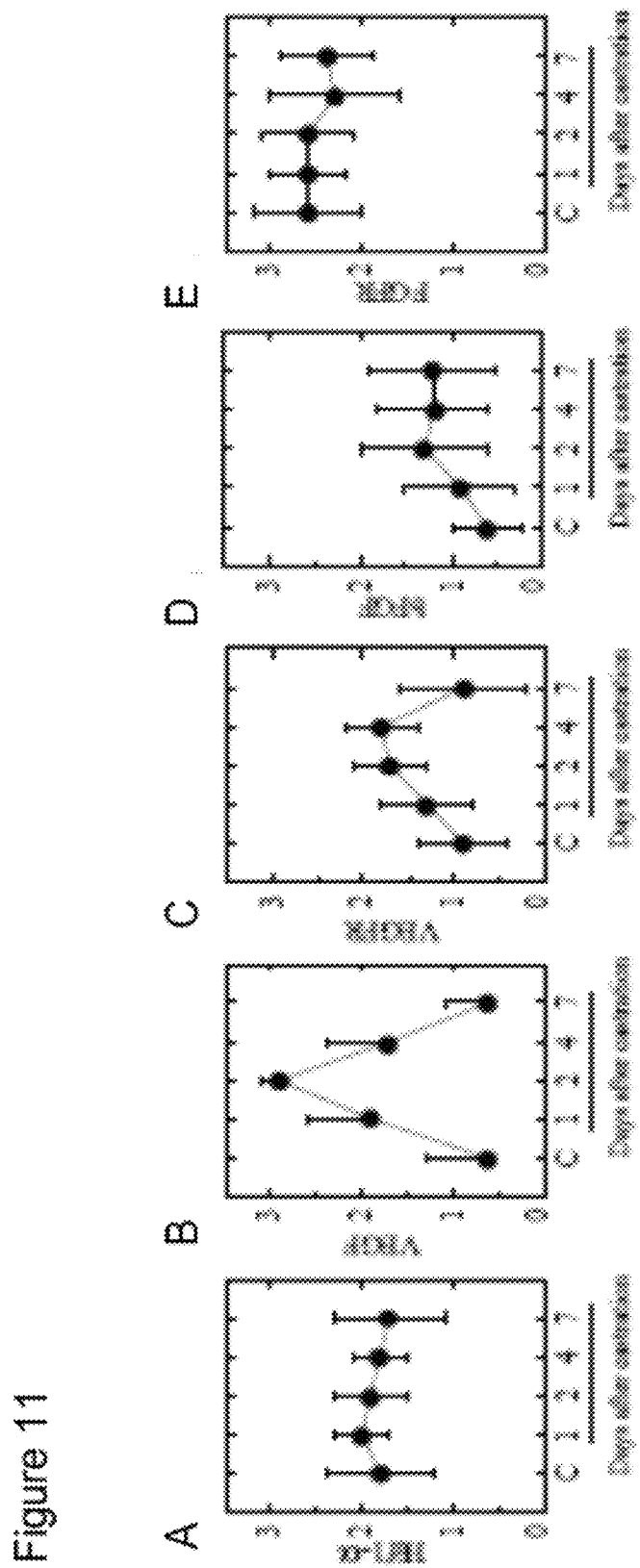
FIG. 11, in panels A-E, provides a graphical summary of the effects of androgen deprivation on various growth hormones in endothelial cells.

The rapid death of human vascular endothelial cells in the prostate xenografts in response to androgen deprivation could have resulted from either a loss of AR-mediated signaling within the vascular endothelial cells, of from loss of AR-mediated paracrine signaling from the tissue microenvironment. AR-mediated paracrine signaling from prostate stromal and epithelial cells may be essential for maintenance of endothelial cell homeostasis, and signaling from the prostate tissue microenvironment is likely to be important in the rapid recovery of the vascular endothelial cell compartment in the absence of androgen signaling following androgen deprivation. A semi-quantitative, IHC-based analysis of levels of expression of angiogenesis-related proteins and steroid receptors in the endothelial, epithelial and stromal cell compartments of the prostate xenografts was developed to characterize changes in the intercellular signaling milieu induced by androgen deprivation. Immunohistochemical staining protocols were optimized for detection and localization of Androgen Receptor (AR), Hypoxia Inducible Factor-1α (HIF-1α), Vascular Endothelial Cell Growth Factor (VEGF), VEGF Receptor-2 (VEGFR-2), basic Fibroblast Growth Factor (bFGF), FGF Receptor-1 (FGFR-1), Platelet Derived Growth Factors (PDGF-AA & PDGF-BB), PDGF Receptor-α (PDGFR-α), Angiopoietin (Ang-1) and the Ang-1 Receptor (Tie-2) protein in the endothelial, epithelial and stromal compartments, as summarized in FIG. 10 and FIG. 11. Several distinct temporal patterns were observed for changes in the protein levels of this group of genes associated with vascular homeostasis and angiogenesis in response to androgen deprivation. HIF-1α, FGFR-1, PDGF-AA and PDGFR-A were expressed at comparable levels in all three prostate cellular compartments, and the pattern of protein expression did not demonstrate temporal changes after androgen deprivation. Ang-1 and Tie-1, genes associated with endothelial cells, were expressed at the highest levels in the endothelial compartment of the human prostate xenografts, but protein levels did not vary in response to androgen deprivation in any of the cellular compartments. VEGF, VEGFR-2, BFGF and PDGF-BB were expressed at higher levels in the endothelial compartment than in the stromal or epithelial compartments, and expression of these proteins demonstrated distinct temporal differences after androgen deprivation. Expression of these angiogenesis-related proteins in endothelial cells peaked on Day 2 after androgen deprivation and returned to baseline levels by Day 7. Comparable temporal patterns for expression were not observed in the other two cellular compartments. AR, in contrast, was expressed at substantial levels in all three prostate cellular compartments before androgen deprivation, protein levels in the endothelial and stromal compartments were reduced dramatically on Days 2 and 4 after androgen deprivation, and expression was largely recovered by Day 7. Trend analysis across time points was performed using a 2-sided application of the Umbrella Test with Unknown Peak (Mack-Wolfe), which tests for single peaks, single dips, continuous increases or continuous decreases. Application of this analysis to the discrete scores for the level of immunohistochemical staining for each prostate cellular compartment averaged across multiple patient specimens provided for quantitative analysis. The trends for temporal changes in levels of endothelial AR, VEGF and VEGFR-2 after androgen deprivation demonstrated statistical significance, with p-values <0.02, while the trends for changes in expression of endothelial bFGF and stromal AR, VEGF, and FGFR-1 approached significance with p-values <0.1. However, the changes approached 90%, despite not achieving the level of statistical significance.

Steroid Receptor Expression in Human Prostate Primary Xenografts During the Two Weeks Following Androgen Deprivation.

IHC-based analysis of the effect of androgen deprivation on the expression of steroid receptors was conducted with antibodies specific for AR, ER-α and ER-β on cohorts of xenografts from 8 patients. The temporal analysis was as described above, but with the addition of time points on Day 14 and Day 28 post-androgen deprivation. ER-α and ER-β proteins were present in endothelial, epithelial and stromal cells of xenografts from intact (non-androgen deprived) hosts at all time points. In animals subjected to androgen deprivation, levels of ER-α and ER-β protein in endothelial cells increased to above pre-androgen deprivation levels by Day 28, while the level of AR protein expression in endothelial cells increased from Day 4 to Day 7, approaching the precastrtion level, and remained mostly unchanged from Day 7 to Day 28. Temporal changes in the pattern of AR expression in both the prostate epithelial and stromal compartments was similar to their expression in the prostate vascular endothelial compartment, exhibiting a decrease at early time points after androgen deprivation, and a recovery to a level higher than the pre-androgen deprivation level by Day 28. Expression of ER-β varied little across the time points after androgen deprivation in either epithelial or stromal cells. In contrast to the temporal pattern of expression of ER-α observed in the vascular endothelial cells, ER-α protein levels in both the epithelial and stromal compartments increased progressively from the pre-androgen deprivation levels, demonstrating levels at Day 28 substantially higher than pre-androgen deprivation levels.

Thus, the short-term primary xenografts of human prostate tissue provide a unique model for identification of agents that take advantage of response of various cellular compartments of the intact human prostate to androgen deprivation. Because of the ability to study xenografts from an individual across multiple time points, or xenografts from multiple patients transplanted to a single host, the invention has utility for characterizing test agents in the signaling milieu induced by androgen deprivation, particularly changes in protein expression of steroid receptors, hypoxia inducible factors, angiogenic factors and their cognate receptors within the vascular endothelial, stromal and epithelial compartments of the human prostate.

Example 3

This Example demonstrates the effects of angiogenesis and androgen deprivation on etiologies of human prostate coagulopathy.

This Example demonstrates that a pro-coagulative environment exists in the highly angiogenic environment of the primary prostate xenografts prior to androgen deprivation, as evidenced by both tissue factor expression by vascular endothelial cells and deposition of fibrin in the vessels and in the perivascular space, and secondly, that androgen deprivation increases significantly the pro-thrombotic state.

The data presented in this Example were obtained using the following materials and methods.

Short Time Point Post-Castration Human Prostate Primary Xenografts (STP-PCX)

Surgically resected prostate tissue was collected in accordance with the National Institutes of Health guideline on the use of human subjects, and with approval by the IRB at The University of North Carolina at Chapel Hill. Human prostate tissue designated as excess tissue was obtained from 8 patients at the time of radical prostatectomy. Gross morphological assessment of the resected prostates by the surgeon was the basis for identification of the specimens as benign, originating from non-involved areas of the surgical specimen. Fresh tissue specimens were submerged immediately in ice-cold ViaSpan solution (Barr Laboratories Inc., Pomona, N.Y.), and transported on ice for transplantation. An initial tissue (IT) specimen, at least 5 $mm^3$, was removed from each surgical tissue sample before preparation for transplantation, the IT fragment fixed in 10% formalin, and the fixed tissue paraffin-embedded for histologic analysis.

Primary xenografts were established from human prostate tissues as described above for Examples 1 and 2. Dual immunohistochemical staining was performed essentially as described in Example 2.

Analysis of Tissue Factor Expression by Cellular Compartment

STP-PCX human prostate primary xenograft specimens were stained by Dual-IHC to label blood vessels and evaluate the expression of tissue factor (TF) by the individual cellular compartments of the prostate xenografts (Endothelium, Epithelium and Stroma). The expression level of TF was evaluated manually for each cellular compartment and assigned an individual score based upon the staining intensity of the chromagen associated with binding of the TF-specific antibody: 0 (no stain), 1 (weak stain), 2 (moderate stain), and 3 (strong stain). The assigned score represented the level of expression in the majority of the cells in each compartment, for each tissue section, at each time point. Two investigators, blinded to the origin of the specimen, scored each slide independently, and the scores were averaged for a composite staining intensity; inter-observer scoring demonstrated satisfactory concordance (Pearson's R=0.65, R Squared=0.43, P=<0.0001 and Spearman R=0.65, P=<0.0001).

Analysis of Tissue Factor Expression and Fibrin Deposition by Vascular Endothelial Cells.

STP-PCX human prostate primary xenograft specimens were stained by Dual-IHC to evaluate the expression of tissue factor (TF) by vascular endothelial cells and pattern of fibrin deposition relative to the prostate vasculature. Vessels were segregated into three groups; 1) vessels that demonstrated positive staining for the combined endothelial cell markers CD31 and CD34, 2) vessels that demonstrated staining for CD31/CD34 and expression of TF, and 3) vessels that demonstrated staining for CD31/CD34 and close association with fibrin/fibrinogen. The MVD (total labeled vessels per field), TFEI (percentage of vessels labeled with both vascular endothelial cell and tissue factor markers per field) and FAI (percentage of vessels labeled with vascular endothelial cell markers and associated with intra- or perivascular fibrin deposition per field) were calculated from the manual counts and the standard error of the mean (SEM) was calculated for each time point for each treatment group.

Statistical Analysis

The statistical analyses performed to describe the data presented in this Example included: 1) The Area-Under-the-Curve-with-respect-to-Ground (AUCG) test, for the comparison of general time course trends between xenografts from androgen deprived host animals versus mock castrated hosts, 2) The ANOVA or Kruskal-Wallis variance analysis test, to evaluate inter-treatment effects (androgen deprived versus mock castrate) over time with Bonferroni or Dunn pair wise post-tests, respectively, to identify days where the difference in the measured endoints were significant, 3) The Student t-Test or Wilcoxon Signed Rank Test, for evaluation of intra-treatment effects in day pairings within either the castrate or mock castrate groups (482). Descriptive statistical analyses including: median, mean, count, standard deviation and normality testing (Shapiro-Wilk and Kolmogorov-Smirnov with Dallal-Wilkinson-Lilliefor P value) were performed to confirm or reject the assumption of a Gaussian distribution and to determine whether parametric or nonparametric tests should be employed.

Multiple xenografts from each patient were generated by dissection of the surgical specimen, and the xenografts were implanted simultaneously into a cohort of animals. This approach allowed comparisons by patient, by time point, and by condition, and the 5% alpha value applied to the paired Student t-tests or Wilcoxon Signed Rank tests could be divided by the total possible pairings to take a family-wise effect approach to the statistical analysis. However, specimens for analysis at sequential time points for a single patient were grown in separate mouse hosts, suggesting a pair-wise application of the 5% alpha for each test. Significant pair-wise P values are indicated in the results, and the P value necessary for a family-wise effect are provided for comparison. The mean values at different time points were capable of increasing or decreasing, therefore, two-tailed tests were applied throughout the analysis. Descriptive statistics, normality testing, Student Paired t-Tests and Wilcoxon Signed Rank tests were performed using Prism 4 version 4.03 (GraphPad Software, Inc., San Diego, Calif.). ANOVA, Kruskal-Wallis and correlation tests were performed using InStat version 3.06 (GraphPad). Power and Sample Size analysis was performed using StatMate2 version 2.00 (GraphPad). Standard Error of the Mean (SEM) and Area Under the Curve with respect to Ground (AUCG) calculations were performed with Microsoft Excel 2003 (Microsoft Corp., Redmond, Wash.). All data were graphed ±SEM.

The results obtained by using the foregoing materials and methods described in this Example are as follows.

Tissue Factor Expression in Primary Xenografts of Human Prostate

Dual IHC with antibody markers of vascular endothelium and tissue factor allowed semi-quantitative analysis of the intensity of tissue factor expression in the individual cellular compartments of the prostate at sequential short time points following androgen deprivation. On a semiquantitative scale (0—Negative, 1—Weak, 2—Moderate, and 3—Strong), no significant differences in tissue factor staining intensity were observed for any of the prostate cellular compartments over the seven days following mock castration, when comparing intra-treatment time points (Day 0-Day 2, Day 0-Day 7 and Day 2-Day 7) (t-Tests, P>0.05; Wilcoxon tests, P>0.05). The epithelium of xenografts harvested from androgen-deprived hosts stained more intensely for Tissue Factor than the epithelium from intact hosts throughout the period of androgen deprivation, even at Day 0 after as little as two hours of androgen deprivation. There was a significant difference between tissue factor staining intensity in epithelial cells in xenografts harvested from the androgen deprived mouse host cohort compared to xenografts from the mock castrate host cohort (AUCG: t-Test, P=0.0419; Wilcoxon P=0.1250. However, inter-Treatment variance analysis (ANOVA and KW-Dunn) did not demonstrate a significant difference in xenograft tissue factor staining intensity between xenografts from androgen-deprived and mock castrate mouse hosts (Inter-Treatment: ANOVA, P=0.4618; KW-Dunn, P=0.4861).

Tissue factor staining intensity in endothelial cells in xenografts from mock castrate hosts remained essentially negative (Score <1.0) for the seven days following mock castration. In contrast to the increased expression of tissue factor in epithelial cells harvested within two hours of androgen deprivation, tissue factor expression in endothelial was not enhanced at the Day 0 time point. However, tissue Factor expression in endothelial cells in xenografts from castrate hosts increased markedly between Day 0 and Day 2, and decreased back to near the level observed at Day 0 by Day 7 after androgen deprivation. Statistical comparison of tissue factor expression between xenografts from mock castrate and castrate hosts failed to demonstrate significant differences (AUCG) and inter-treatment effect (ANOVA) for the endothelial cells by time point. Inter-treatment (t-Test and Wilcoxon) analysis of endothelial tissue factor expression failed to demonstrate significant difference between day pairs within xenograft bearing host cohorts that were either castrated or mock castrated.

Tissue factor staining intensity in the stromal compartment of the prostate xenografts from mock castrate hosts was negative to weak (score approximately 0.7) from Day 0 to Day 2, then decreased from Day 2 to Day 7 (score approximately 0.3). Tissue factor staining intensity in xenografts from castrate hosts was negative to weak (score approximately 0.7) at Day 0, increased to weak (score approximately 1.0) at Day 2 and decreased to negative to weak (score approximately 0.7) at Day 7. Statistical analysis of stromal tissue factor staining intensity for general trend comparison (AUCG), intra-treatment differences in mean intensity or inter-treatment differences by timepoint did not identify significant differences. These results indicate that there may be a difference in stromal tissue factor expression in xenografts from mock castrate hosts compared to xenografts from castrate hosts.

Tissue Factor Expression in Blood Vessels

Dual-IHC with antibodies specific for markers of vascular endothelium and tissue factor allowed manual quantification of vessels that were positive, or negative, for tissue factor expression as visualized as endothelial cells that expressed endothelial markers only, or expressed endothelial markers and tissue factor. Although a gradual decrease in the Tissue Factor Expression Index (TFEI) was observed across the seven days following mock castration, the change was not statistically significant in pair-wise intra-treatment analysis; however, the Day 0 to Day 2 comparison approached significance (t-Test, P=0.0529; Wilcoxon, P=0.0653). In contrast, androgen deprivation induced a significant increase in the TFEI from Day 0 to Day 2 and decrease from Day 2 to Day 7, returning to near initial levels (t-Test, P=0.0529). Approximately 40% of vessels in xenografts from mock castrate hosts, and at least 70% of vessels in xenografts from castrate hosts, were positive for tissue factor expression at Day 0, and throughout the seven days following androgen deprivation.

Additionally, there was a significant difference in the tissue factor expression index (TFEI) in xenografts from androgen deprived hosts compared to those from mock castrate hosts as indicated by the general trend analysis (AUCG) and inter-treatment variance analysis (KW-Dunn) (AUCG: t-Test, P=0.0060; Wilcoxon P=0.0625 and Inter-Treatment: KW-Dunn, P=0.0252). Further, the TFEI increased significantly from Day 0 to Day 2 and appeared to decrease from Day 2 to Day 7 in xenografts from androgen deprived mouse hosts (Castrate Day 0-Day 2 t-Test=0.0184). These results indicate that androgen deprivation induces a transient increase in human prostate xenograft endothelial cell tissue factor expression, a marker correlated with endothelial cell damage.

Fibrin Deposition in Association with Prostatic Vasculature

At sites of vascular damage, fibrinogen can leak into the perivascular interstitial space, or remain in the lumen of the vasculature, and be cleaved to form fibrin. Dual IHC with antibodies specific for markers of vascular endothelium and fibrin/fibrinogen allowed manual quantification of vessels that were, or were not, associated with intravascular or perivascular fibrin deposition. No significant change in the Fibrin Association Index (FAI) was observed across the seven days following mock castration, as indicated by the intra-treatment analysis (t-Test and Wilcoxon). However, in xenografts harvested from androgen-deprived hosts there was a significant increase in the FAI from Day 0 to Day 2, and decrease from Day 2 to Day 7 (Day 0-Day 2: Wilcoxon, P=0.0234; Day 2-Day 7, Wilcoxon, P=0.0547). Additionally, there was a significant difference in FAI comparing the androgen deprived mouse host cohorts to the mock castrate host cohorts, as indicated by the general trend analysis (AUCG) and inter-treatment variance analysis (ANOVA and KW-Dunn) (AUCG: t-Test, P=0.0024; Wilcoxon P=0.0625 and Inter-Treatment: ANOVA, P=0.0001; KW-Dunn, P=0.0001). Finally, at least 35% of vessels in xenografts from mock castrate hosts and at least 55% of vessels in xenografts from androgen-deprived hosts, were associated with fibrin deposition at Day 0 and throughout the seven days following androgen deprivation. These results indicate that androgen deprivation induces a transient increase in fibrinogen extravasation and fibrin deposition in human prostate xenografts.

Example 4

This Example provides a characterization of transition of the prostate tissue microenvironment, and specifically endothelial cells, from a predominately androgen (T) regulated microenvironment to one where the role of androgen is de-emphasized, and the role of other growth factor signaling pathways such as the hypoxic response and estrogen (E) assume greater regulatory roles in the absence of testicular androgens.

Angiogenesis: During xenograft establishment the tissue microenvironment is androgenic due to the presence of testicular androgen and the supplemental testosterone pellet. The testosterone/estrogen ratio (T/E) is in favor of T. VEGF and PDGF-AA expression is elevated in the epithelium, and bFGF expression is elevated in the stroma. Consequently, the combination of DHT, VEGF, PDGF-AA and bFGF provides the pro-angiogenic signals that drive the increase in MVD during xenograft engraftment.

Vascular Involution: During the two days immediately following androgen deprivation, the pattern of expression of pro-angiogenic peptides by the stroma and epithelium in the androgenic environment changes to one where bFGF expression by epithelial cells and PDGF-AA expression by stromal cells has increased in the absence of androgen. However, the MVD decreases during this interval even though expression of the pro-angiogenic peptides bFGF and PDGF-AA is increasing. One possible explanation is that the bFGF protein may remain intracellular, and have no paracrine effect. The change in the source of PDGF-AA from epithelial to stromal cells may indicate a change in role of the peptide. Stromal cell proximity to endothelial cells may allow PDGF-AA to support the endothelial cell VEGF-VEGFR autocrine survival loop by the significant increase in both by Day 2 post-androgen deprivation. From the time of androgen deprivation, the T/E ratio is likely to be in favor of E.

Vascular Rebound: From Day 2 to Day 7 following androgen deprivation the pattern of expression for pro-angiogenic peptides by the stroma and epithelium returns to the pattern evident during the interval of active angiogenesis. Expression of VEGF and PDGF-AA by epithelial cells, and of bFGF by stromal cells, is increased in concert with the increase in MVD. This suggests that the surviving endothelium responds to increased expression of pro-angiogenic peptides by epithelial and stromal cells, facilitating vascular rebound or recovery.

Stabilization: From Day 7 to Day 28 following androgen deprivation the expression of AR, ER-α and ER-β changes in all of the cellular compartments. Endothelial cell expression of pro-angiogenic ER-α, and anti-angiogenic ER-α, increased during vascular stabilization, while expression of the pro-angiogenic AR remained mostly unchanged. This balance of AR and ER mediated signaling may favor continuing vascular expansion. In response to androgen deprivation, expression of AR and ER-β in the epithelial compartment increased appreciably, while ER-α expression was lost, the net result of which may favor epithelial proliferation. Finally, stromal AR and ER-β expression did not change appreciably during vascular stabilization, while expression of ER-α increased dramatically, the net result of which may limit expansion of, or decrease the size of, the prostate stroma. As discussed in Chapter 3, in the adult prostate, AR is a mitogen for all three prostatic cell types. However, ER-β signaling represents a mitogenic signal for prostate epithelial, stromal and vascular endothelial cells, while ER-α signaling mediates quiescence (43, 44, 400).

Based upon the steroid receptor expression profile for each of the cellular compartments observed in the prostate xenografts, after Day 28 under continued androgen deprivation, the endothelium could receive mitogenic signaling from the interaction of androgens and estrogens with AR and ER-β, and quiescence signaling from the interaction of estrogens with ER-α. These data indicate that the molecule that leads the response is naturally present, essentially assuring re-growth of the cancer.

As also can be seen by the foregoing, the human prostate primary xenografts represent a valuable model for translational research because the tissue retains all the components of the human prostate microenvironment, the in vivo tissue architecture and human pathophysiology, and androgen responsiveness. This unique model has provided at least three important but non-limiting observations of the human prostate tissue microenvironment: 1) there is a transient, short window (4-7 days) immediately following androgen deprivation in which the integrity of the prostate microvasculature is compromised; 2) androgen-sensitive human endothelial cells rapidly develop an alternative mechanism(s) for maintaining homeostasis and regenerating the microvascular network in the absence of androgen; and 3) androgen deprivation results in up-regulation of VEGF-A by specifically the prostate endothelial cells, potentially creating autocrine-mediated growth that would be insensitive to anti-VEGF therapy. A comparable androgen independent revascularization was not observed in rat prostate. The difference in the response of rat prostate and the human prostate tissue xenografts could result in missed opportunities for identification of more effective treatments for BPH or advanced CaP. It is believed that the transient window of vascular perturbation presents an optimal timeframe for the administration of therapeutic modalities that target prostate cancer epithelial cells with enhanced therapeutic efficacy, or of anti-angiogenic adjuvant therapies focused on preventing the restoration of microvascular integrity. The model is also suitable for testing any agent as a candidate for treating human prostate cancer or benign prostatic hyperplasia.

Example 5

For the following Examples, primary xenografts of human benign and CaP tissue transplanted to immunocompromised SCID mice were utilized to characterize the response of the prostate vasculature during the initial fourteen days of AD. Microvessel density and vascular lumen diameter in the prostate xenografts decreased rapidly after AD, reached a nadir on Days 2-4, and recovered between Days 4-14. The number of apoptotic endothelial cells peaked on Day 2 after AD, and decreased to pre-castration levels over Days 4-7. Leakage of vascular contents into the interstitial space was apparent between Days 1-3 after AD, however, the vascular permeability barrier re-established between Days 7-14. Expression of VEGF-A, VEGFR-2, and bFGF protein increased in endothelial cells between Days 2-4 after AD, which preceded vascular recovery and appeared to be a direct and specific response of the endothelial cells to AD. Lack of comparable up-regulation of these genes in primary cultures of human prostate endothelial cells in response to AD suggests a role for paracrine signaling mediated through stromal or epithelial cells. We have discovered that VEGF-A expression by prostate endothelial cells appears to represent a key facilitator of the vascular rebound in human prostate tissue induced by removal of circulating testicular androgens.

The following provides a description of the materials and methods used in obtaining the results disclosed in Example 6.

Human Prostate Primary Xenografts: Prostate tissue was collected in accordance with National Institutes of Health guidelines on the use of human subjects, with approval by the IRBs at The University of North Carolina at Chapel Hill (UNC) and Roswell Park Cancer Institute (RPCI). Human prostate tissue samples were obtained by radical prostatectomy from at least 8 different patients. Prostate tissue was dissected out by a pathologist and designated as benign (non-involved) and tumor tissue using a known technique. The majority of these patients were adult men over 55 years old. Gleason grade in these patients varied between 3+3 to 4+3. None of the patients had undergone treatment of BPH or hormonal therapy prior to surgery. Tissue specimens were submerged immediately in ice-cold ViaSpan solution (Barr Laboratories Inc., Pomona, N.Y.), and transported on ice for transplantation. An initial tissue (IT) specimen of at least 8 $mm^3$ was removed from each surgical tissue sample before transplantation, fixed in 10% formalin, and paraffin-embedded for histologic confirmation of the tissue as benign or malignant.

Primary xenografts of freshly harvested human prostate tissues were established in SCID mice essentially as described in U.S. patent application Ser. No. 12/011,929. All experimental protocols that involved laboratory animals were performed in accordance with the National Institutes of Health guidelines and were approved by the Institutional Animal Care and Use Committee at UNC and RPCI. In brief, the tissue specimen was cut into wedge-shaped pieces 2-3 mm in length, and 1-2 mm in width at the broadest end, and the wedges were transplanted into male SCID mice, 3 months of age, that previously had been castrated and implanted subcutaneously with a 12.5 mg sustained-release testosterone pellet (Innovative Research of America, Sarasota, Fla.) to maintain serum testosterone levels at ~4.0 ng/ml throughout the study. For implantation of prostate tissue, small (~3 mm) incisions were made in the skin on the right and left flanks of immunocompromised mouse hosts anesthetized with Domitor (1 mg/kg i.p.) (Pfizer, Inc., New York, N.Y.), tissue wedges to be implanted were dipped in Matrigel™ (BD Biosciences, Bedford, Mass.), and the coated tissue wedges were inserted into the subcutaneous space through a 10 gauge trocar device (Popper & Sons, Inc., Lincoln, R.I.). Between 3 and 5 wedges from each patient were implanted along each flank through individual incisions, with up to 10 fragments transplanted per animal. Incision sites were closed with Nexband tissue glue (Veterinary Products Laboratories, Phoenix, Ariz.).

Androgen deprivation (ADT) was initiated by removal of the testosterone pellet 1 month after transplantation of prostate tissue. Xenografts from control hosts (Day 0) were harvested from animals euthanized prior to removal of the testosterone pellet. For analysis of the effects of androgen deprivation, animals were euthanized and xenograft tissues collected on Days 1, 2, 4, 7, 10 and 14 after androgen deprivation. Harvested xenografts were fixed in 10% formalin for a minimum of 24 h, after which the fixed tissues were paraffin-embedded. Paraffin blocks were sectioned (5.0 μm) onto ProbeOn Plus slides (Fisher Scientific International, Suwanee, Ga.).

Prostate Tissue Digestion and Primary Cell Culture: Primary cultures of HPEC were prepared using a Dynabead-based methodology (DYNAL Biotech ASA, Oslo, Norway according to known techniques. Fresh surgical specimens of prostate tissue were minced into 8 $mm^3$ pieces and digested with dispase (2.4 U/ml, Invitrogen Corporation, Carlsbad, Calif.) for 16 h at 4° C. The heterogeneous tissue hydrolysate was cultured for approximately 1 week in endothelial growth media (Endothelial cell growth medium MV, Promocell, Heidelberg, Germany) supplemented with 5% fetal calf serum, at 37° C. in 5% $CO_2$. After 1 week in culture, HPEC were isolated using anti-CD31-conjugated magnetic beads, and cultured in endothelial growth media for no more than 6 passages before experimental studies were performed.

Immunostaining Analysis: Histological specimens were prepared from each IT specimen harvested from the tissue specimen before implantation, and from all corresponding xenograft specimens, and one section from each block was stained with AMACR (racemase) to assess the presence of CaP. Complete specimen sets were available for 8 patients that contained IT specimens and xenograft specimens of matched benign and CaP tissue harvested at all the Short Time Points After Castration (STP-ACX) (Days 1, 2, 4, and 7). Each specimen set included an AMACR stained IT specimen and AMACR stained specimen from xenografts harvested at all time point. Individual sections from each specimen were characterized using immunohistochemistry to establish the pattern of expression of an apoptotic marker (cleaved caspase-3), endothelial cell markers (CD31 and CD34) and angiogenesis-related proteins. Species-specificity of the anti-human CD31 antibody was confirmed by immunohistochemistry using formalin-fixed, paraffin-embedded human or mouse prostate tissue.

Tissue sections were de-paraffinized using Citrasolv (Fisher), hydrated through graded washes of ethanol and de-ionized water, and equilibrated in automation buffer (Biogenex, San Ramon, Calif.). Antigens were retrieved by boiling the slides in 10 mM citric acid buffer (pH 6.0). Endogenous peroxidase activity and background avidin-biotin reactivity were blocked according to the manufacturer's protocol (Vector Laboratories, Inc., Burlingame, Calif.) prior to quenching of non-specific antibody binding with Power Block (Biogenex, Jackson, Wyo.). Blocked sections were incubated with antigen-specific primary antibodies at optimized dilutions in common antibody diluent (Biogenex) for 30 minutes at 37° C., followed by incubation for 20 minutes at 37° C. with a biotinylated secondary antibody matched to the host species of the primary antibodies. Immunoreactive target antigens were visualized using Vectastain Elite ABC Immunoperoxidase Kit (Vector) with DAB (Vector or Sigma, St. Louis, Mo.), NovaRed (Vector), Histomark Black (KPL, Inc., Gaithersburg, Md.) or True-Blue (KPL) peroxidase chromagen kits according to each manufacturer's protocol. Slides were counterstained with Methyl Green (Sigma) to identify nuclei, dehydrated with ethanol, and mounted with Vectamount (Vector). Sections of BPH tissue were included in all staining procedures as a positive control, and primary antibody was omitted as a negative control.

Analysis of Expression of Angiogenic Factors: STP-ACX human prostate primary xenograft specimens were immunostained for expression of selected angiogenesis-related factors (VEGF-A, bFGF, PDGF-AA, PDGF-BB and Ang-1), their cognate receptors (VEGFR-2, FGFR-1, PDGFR-α/β, and Tie-2), and Hypoxia Inducible Factor-1 alpha (HIF-1α) (Table 1). Expression of the individual proteins in the epithelial, endothelial, and stromal compartments were scored independently, with the levels of expression evaluated manually in blinded specimens. The scoring system was based upon the intensity of staining: 0 (no stain), 1 (weak stain), 2 (moderate stain), and 3 (strong stain). The assigned score represented the level of expression in the majority of the cells in each prostate cellular compartment. Levels of expression were scored at each time point after androgen deprivation for multiple microscopic fields from each xenograft for each patient; and scores were averaged across all samples from all patients at each time point. Two investigators, blinded to the origin of the specimen, scored all slides independently and the scores were averaged for a composite staining intensity. Inter-observer scoring of the levels of protein expression demonstrated significant concordance (r=0.90).

Reverse Transcription, PCR and Quantitative Real-Time PCR: Total RNA from primary cultures of HPEC was prepared using the RNAeasy mini-kit (Qiagen, Valencia, Calif.). Reverse transcription from mRNA was performed using the SuperScript™ III First-Strand kit (Invitrogen, Carlsbad, Calif.). Approximately 1.0 μl of the reverse transcribed cDNA product was used as template in the Platinum PCR Supermix (Invitrogen) reaction mixture that contained 200 nM of each primer. PCR products were separated by electrophoresis in 2% agarose gels and visualized with ethidium bromide. Glyceraldehyde-3-phosphate dehydrogenase (GAPDH) was used as a loading control in analytical gels. Quantitative real-time PCR (QRT-PCR) was performed using power SYBR Green PCR Master Mix (Applied Biosystems, Foster City, Calif.) according to the manufacturer's instructions in the ABI PRISM 7300 system. For each sample, triplicates of 25 μl reactions were prepared using 2×SYBR Green PCR Master Mix (Applied Biosystems) along with 1.5 μl of cDNA and 200 nM of each primer. The reactions were performed in 96 well ABI Prism (Applied Biosystems) optical reaction plates capped with optical caps. PCR product levels were measured continuously using the ABI7300 system during 40 cycles.

Digital Image Collection and Analysis: Digital images of sections immunohistochemically stained for cleaved caspase-3 and angiogenesis-related proteins were collected using a Kontron ProgRes 3012 camera (TriPath Imaging, Inc., Burlington, N.C.) mounted on an Axioskop microscope (Carl Zeiss, Inc., Thornwood, N.Y.) at 100×, 200×, 400× and 630× magnification, depending on the intended use of the images. Image analysis for manual counts of objects was performed using ImageJ software with the Cell Counter Plug-In (Research Services Branch, National Institute of Mental Health, Bethesda, Md.). Three 100× (0.480 $mm^2$), 200× (0.120 $mm^2$) or 400× (0.030 $mm^2$) fields were collected and analyzed. Investigators were blinded to the origin of the specimen for all manual scoring of histological specimens. Digital images of immuno-histochemically stained sections for the endothelial cell markers CD31/CD34 were collected using a Hamamatsu Color Chilled 3CCD camera (Hamamatsu, Bridgewater, N.J.) mounted on an Axioskop microscope (Carl Zeiss) at total magnification 400×. Five images (0.4 $mm^2$) were analyzed to determine the average number of vessels per field (microvessel density, MVD).

Analyses of Vascular Integrity: Measurements of vessel lumen diameter were made using Image Pro Plus 5.0 (Media Cybernetics, Inc, Bethesda, Md.). Lumen diameter was measured by drawing a line from the abluminal side of one end of the immunostained CD31/CD34 vessels to the opposite abluminal side. Lumen diameter at each time point after androgen deprivation (Day 1, Day 2, Day 4, Day 7, Day 10 and Day 14) was compared to the control lumen diameter (Day 0) measurement using student t-tests. Vascular leakeage after androgen deprivation was evaluated in primary xenografts using intra-vital binding of lectin administered systemically using know methods. Briefly, mice bearing xenografts were anesthetized with ketamine (100 mg/kg i.p.) plus xylazine (10 mg/kg i.p.). Biotin-labelled *L. esculentum* lectin (100 µl of 1.0 mg/ml in 0.9% NaCl, Vector Laboratories) was injected into the tail vein and allowed to circulate for 5 min. At the conclusion of the incubation, the chest was opened and the vasculature was perfused with a fixative solution (1.0% paraformaldehyde in PBS, pH 7.4) through an 18-gauge cannula inserted into the aorta via an incision in the left ventricle for 2 min at a pressure of 120 mmHg. Blood and fixative exited through an opening cut into the right atrium. Fixed xenograft tissues were removed, frozen in OCT, and processed for immuno-analysis. Antibiotin and anti-fibrinogen (fragments D+E) antibodies were utilized to evaluate vascular permeability using standard immunohistochemical procedures, as described above.

VEGF-A Measurement: The measurement of VEGF-A protein production and secretion was carried out using ELISA (R&D Systems, Minneapolis, Minn.) with affinity-purify antibodies directed against VEGF-A. HPEC were seeded in 24 well plates and grown to confluence using endothelial cell medium (Endothelial cell basal medium supplemented with 5% FBS, Promocell). Twenty-four hours after plating, androgen deprivation was initiated by transfer to endothelial cell medium supplemented with charcoal-stripped 5% FBS. Measurement of VEGF-A production and secretion by HPEC was performed as follows: a 100 µl aliquot was taken from the supernatant of cell cultures at time 0 (control), and at 24 h and 48 h after androgen deprivation. As a functional control, cultures also were exposed to 48 h of androgen deprivation, and were refed with endothelial cell media with charcoal-stripped 5% FBS supplemented with 1 nM dihydrotestosterone (DHT) for an additional 24 h incubation.

Analysis of Serum Testosterone Levels: Serum testosterone levels in host mice were measured using a testosterone enzyme-linked immunosorbent assay (ELISA, Immuno-Biological Laboratories Inc, Minneapolis, Minn.) according to the manufacture's instructions. Briefly, serum was collected from blood obtained by eye puncture, and 25 µl of each serum sample was combined with 200 µl of antibody-conjugate and incubated for 60 min at room temperature. After washing the plate, 200 µl of substrate were added to each well and incubated for 15 min at room temperature. The samples were read at 450±10 nm with a microtiter reader (Bio-Tek Instrument EL800). Testosterone concentrations were determined using a standard curve.

Statistical Analysis Data sets were prepared for statistical evaluation by analyzing the reason for missing values and applying appropriate standard data adjustments to provide values in place of blanks. Temporal analyses of the effect of androgen deprivation on xenografts from a single patient used student t-tests and Wilcoxon Signed Rank tests. Additionally, descriptive statistical analysis, including median, mean, count, standard deviation and normality testing (Shapiro-Wilk and Kolmogorov-Smirnov with Dallal-Wilkinson-Lilliefor P value) were calculated to confirm or reject the assumption of normality for mean comparison tests (students t-test or Wilcoxon Signed Rank test). Both power analysis and sample size estimation were performed to design this study.

Analyses of data sets from castrate hosts in studies with 5-time points/patient (day 0, and days 1, 2, 4 and 7 after castration) utilized a paired two-tailed student t-tests or a Wilcoxon Signed Rank test (95% Confidence) between the 10 possible comparison pairs (Day 0 to Day 1, Day 0 to Day 2, Day 0 to Day 4, Day 0 to Day 7, Day 1 to Day 2, Day 1 to Day 4, Day 1 to Day 7, Day 2 to Day 4, Day 2 to Day 7, and Day 4 to Day 7). Each pair-wise test was performed at 95% confidence and each family-wise test was performed at 99.5% confidence. Analysis of the expression of hypoxia inducible factor-1α and angiogenesis-related factors based upon the intensity scores was performed using a Mack-Wolfe Unimodal Umbrella Test with Unknown Peak, adapted for Two-Sided analysis of p-values (Hollander M W D. *nonparametric statistical methods*. New York: Wiley, 1999, p. 787). The described critical values were used to interpret p-values between 0.02 and 0.2. Descriptive statistics, normality testing, students paired t-tests, Signed Rank tests, and data correlations were performed using Prism 4 (GraphPad Software, Inc., San Diego, Calif.). Power and sample size analysis was performed using StatMate 2 (GraphPad). Standard Error of the Mean (SEM) calculations was performed with Microsoft Excel 2003 (Microsoft Corp., Redmond, Wash.). All data, with the exception of the staining intensity scores, were graphed ±SEM. Additional information concerning the application of missing value substitution, the testing of temporal data and the results of temporal data t-tests, Wilcoxon Signed Rank tests and Mack-Wolfe Unimodal Umbrella testing is provided Tables 2 & 3).

Example 5

This Example described the results of experiments performed using the materials and methods set forth in Example 5.

Figure 13:
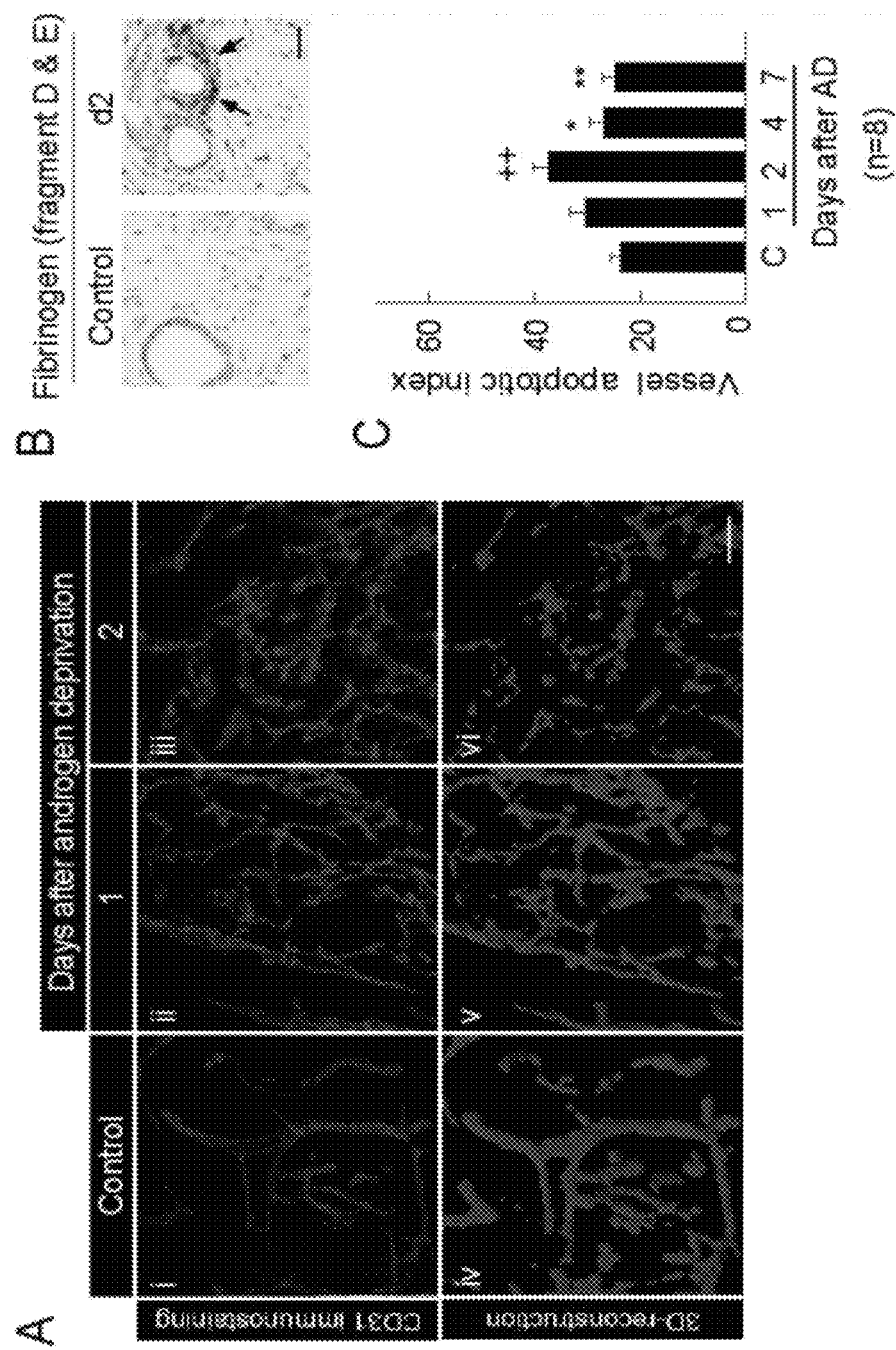
FIG. 13. Acute vascular effect of androgen deprivation in short-term primary xenografts of human prostate tissue. (A) Confocal laser scanning micrographs of blood vessels in primary xenografts of prostate tissue visualized using CD31 immunolabeling on Day 0 (Control, i), and Days 1 (ii) and 2 (iii) after androgen deprivation, and 3D-reconstruction (iv-vi) of the fluorescent immunostaining in serial optical sections (i-iii). Bar: 50 μm. (B) The time of maximal alteration of vascular morphology (Day 2) was concurrent with the time of maximal level of fibrinogen leakage (fragment D and E) into the interstitial tissue space. Bar: 50 μm. (C) Vessel Apoptotic Index indicates the percentage of vessels/field that contained at least one endothelial cell nucleus positive for activated caspase-3 in human prostate primary xenografts on Day 0 (C, control) and Days 1, 2, 4, and 7 after androgen deprivation (AD).

Androgen Deprivation Induces Acute Vascular Damage in Human Prostate Xenografts. The initial goal of this study was to determine if androgen deprivation (castration of the host and removal of the supplementary testosterone pellet) would induce an acute response in the AR-expressing human prostate microvascular endothelial cells in primary xenografts of human prostate tissue, as has been demonstrated in rat prostate in which the endothelial cells are AR-negative. Confocal laser scanning microscopy (CLSM) imaging was performed on CD31 immuno-stained thick sections (100 µm) obtained from primary xenografts of prostate tissue harvested on Days 0 (control), 1 and 2 after androgen deprivation (FIG. 13Ai-iii). 3D-reconstruction of the fluorescent staining in serial optical sections was achieved using Imaris software (Bitplane Inc, St. Paul, Minn.) (FIG. 13Aiv-vi). Marked perturbation of the prostatic vasculature was apparent on Day 2 after androgen deprivation (FIG. 131A). Alteration of the structure of the prostate vasculature correlated with leakage of fibrin/fibrinogen into the interstitial tissue space visualized by IHC, which suggested compromise of the endothelial cell vascular barrier and induction of vascular leakage (FIG. 131B). To confirm that vascular damage induced by androgen deprivation was a direct result of perturbation of endothelial cells, endothelial cell apoptosis was analyzed by quantitation of vessels containing caspase-3-positive human endothelial cells versus total number of vessels (as determined by a combination of CD31 and CD34 immuno-staining). The vessel apoptotic index (VeAI) demonstrated a significant trend that was the inverse of the changes observed in microvessel density (MVD), with a nearly two-fold increase in VeAI between Day 0 to Day 2, followed by a significant decrease from Day 2 to Day 4, and from Day 2 to Day 7 (FIG. 13C, Table 2).

Figure 14:
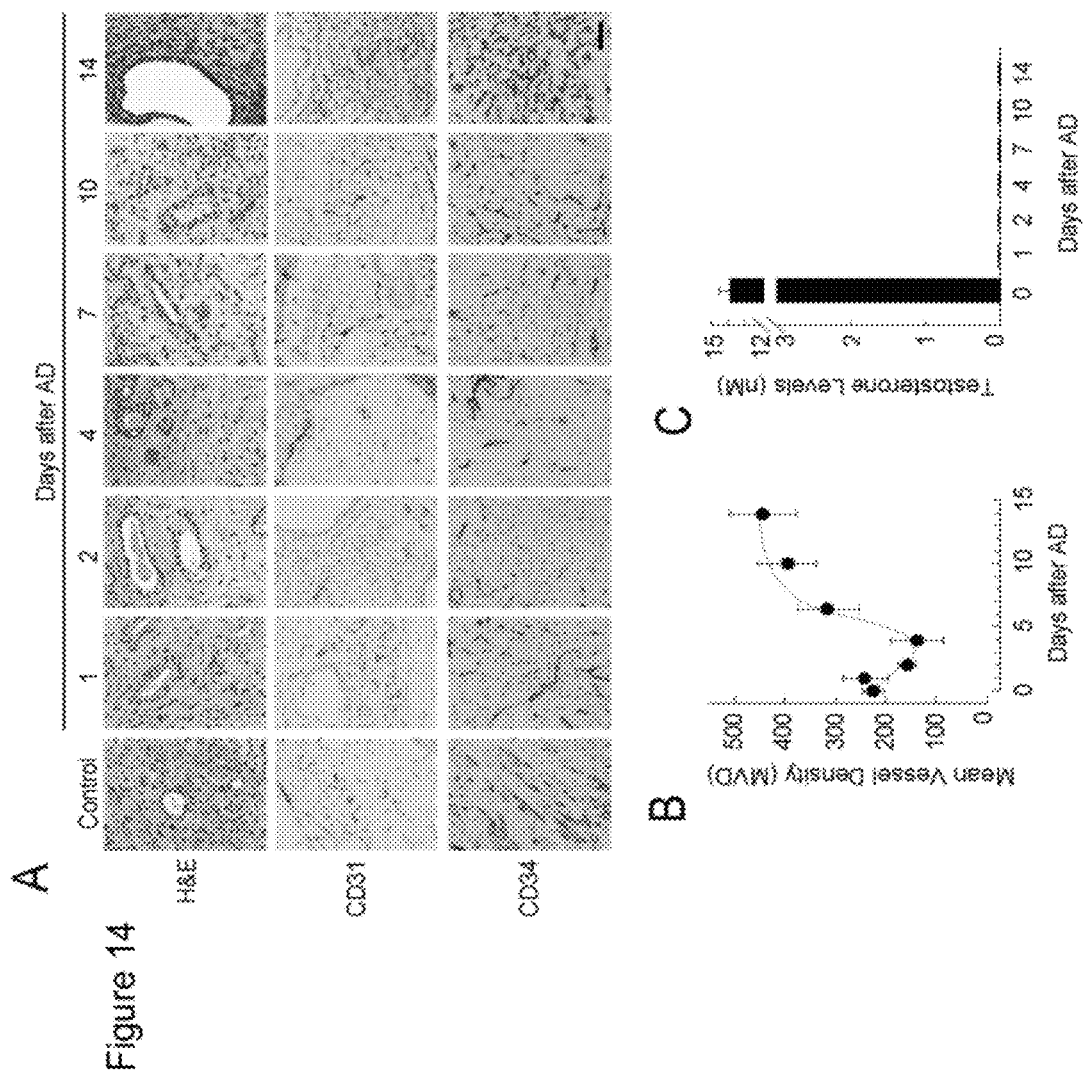
FIG. 14. Time course of changes in vascular structure during the two weeks after androgen deprivation in short-term human prostate primary xenografts. (A) H&E staining of tissue sections obtained from xenografts harvested before androgen deprivation (Control) and on Days 1, 2, 4, 10, and 14 after androgen deprivation. Human prostate tissue architecture was maintained in xenografts after androgen deprivation. Endothelial cells were labeled individually with either anti-human CD31 (1:20, DAKO) or anti-CD34 (1:50, Neomarkers, Fremont, Calif.) antibody, or stained with a combination of anti-human CD31 and anti-CD34 specific antibodies (not pictured), for vessel visualization and quantitation in histologic sections of primary xenograft from untreated (Control) animals and animals on Days 1, 2, 4, 7, 10, and 14 after androgen deprivation. Bar: 50 μm. (B) Micro Vessel density (MVD) in tissue samples of primary xenografts from control (day 0) and androgen-deprived animals harvested on Days 1, 2, 4, 7, 10 and 14 after androgen deprivation. (C) Testosterone levels measured in the serum of control (Day 0) and androgen-deprived animals (Days 1, 2, 4, 7, 10, and 14 after androgen deprivation).

Androgen Deprivation-Induced Prostate Vascular Damage is Followed by a Complete Recovery of the Vasculature. Normalization of the prostate vasculature within the rat prostate after androgen deprivation required introduction of exogenous androgen into castrated animals. The ability of the human prostate vasculature damaged by androgen deprivation to recover in the absence of androgen was analyzed to determine if re-vascularization required androgen stimulation, as in rat prostate. Rodents are an ideal model to analyze the effect of androgen deprivation since, unlike humans, they produce very low levels of circulating adrenal androgen that can become an alternative source of DHT after removal of testicular androgen by castration. An extended morphological and immuno-histochemical analysis of the effect of castration on MVD was conducted in primary xenografts of human prostate tissue at Day 0 and Days 1, 2, 4, 7, 10 and 14 after androgen deprivation. Apoptosis in the prostate epithelial cell compartment increased progressively after androgen deprivation, peaking at Day 7. During this interval, Hematoxylin and Eosin (H&E) staining demonstrated that tissue architecture of the human prostate glandular and stromal compartments was maintained unaffected in xenografts throughout the 14 days of the experiment (FIG. 14A). The MVD in prostate xenografts fell to a nadir on Day 2 after androgen deprivation, however, the MVD began to recover on Days 4-5 after androgen deprivation, and continued to increase through Days 10-14 after androgen deprivation (FIG. 142A-B). The effect of androgen deprivation on prostate endothelial cells was characterized by quantitation of vessels labeled by CD31 or CD34 individually (FIG. 142A) and by total MVD (CD31+CD34; FIG. 142B) in primary xenografts of human prostate tissue. Pair wise analysis of MVD between time points failed to demonstrate statistical significance; however, the data suggested a nadir of MVD occurred between Days 1 to 2 after androgen deprivation, and a rebound by Days 5-7 to nearly the pre-castration MVD. Furthermore, MVD increased beyond pre-castration levels, and by Day 14 attained levels almost twice the level present on Day 0 (FIG. 142A-B). In contrast, while pair-wise analysis of the epithelial cell apoptotic index (EpAI) failed to demonstrate statistical significance, the data suggests a progressive increase in epithelial cell apoptosis from Day 0 to Day 7 (Table 2). Consequently, recovery of the microvasculature was established before the time apoptotic death of the epithelial cells reached maximal levels. Quantitation of circulating testosterone levels on Day 0, and Days 1, 2, 4, 7, 10 and 14 after removal of the testosterone pellet, confirmed that castration and removal of the supplemental testosterone pellet induced a state of permanent androgen deprivation (FIG. 142C). ELISA analysis demonstrated a rapid reduction of circulating testosterone to 0.01 nM, and that this level was maintained throughout the 14 days of the experiment.

Figure 15:
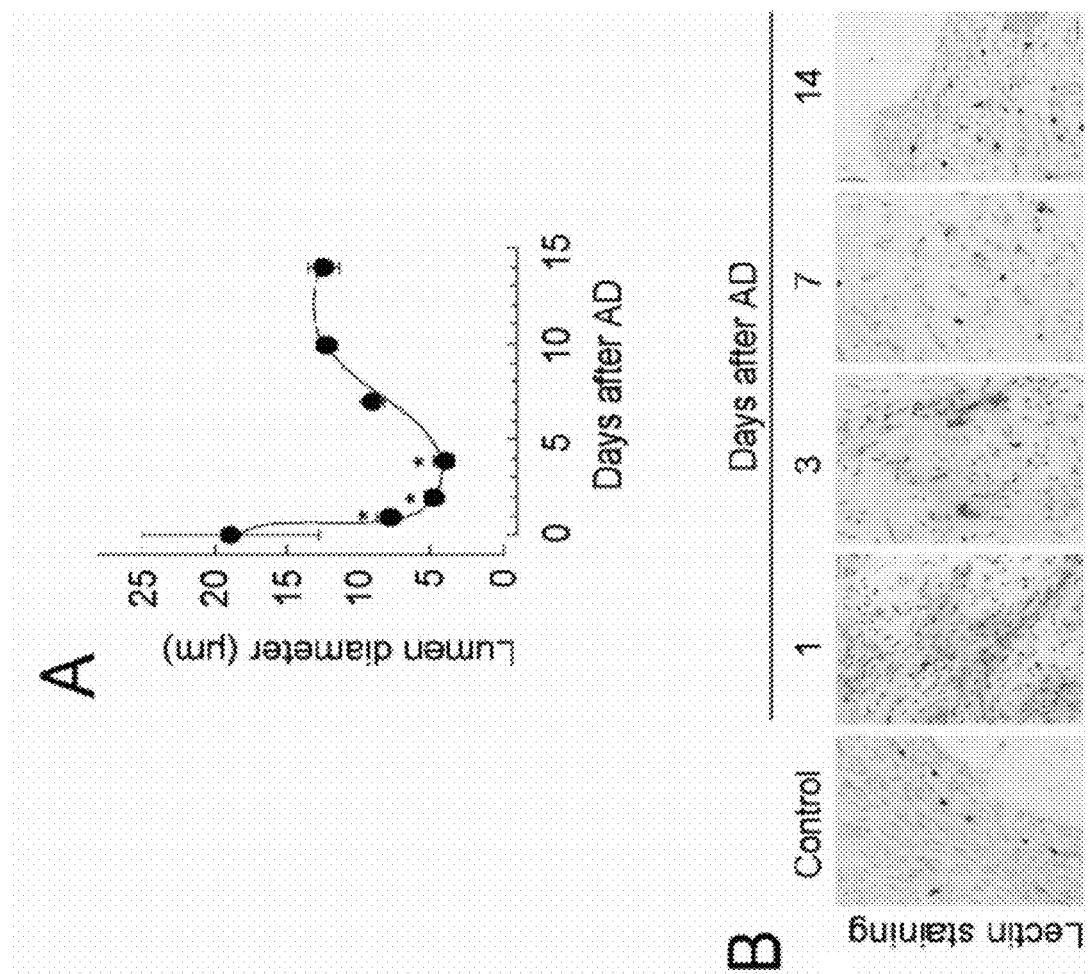
FIG. 15. Effect of androgen deprivation on vascular lumen diameter and vascular integrity. (A) Measurement of vascular lumen diameter on Day 0 and Days 1, 2, 4, 7, 10, and 14 after androgen deprivation. Lumen diameter was estimated by drawing a line from the abluminal side of one end of vessels immunostained with CD31/CD34 to the opposite abluminal side. Lumen diameter measurements at each time point after androgen deprivation were compared to the lumen diameter measurement in controls (Day 0) using student t-tests. Lumen diameters measured at Day 1, Day 2, and Day 4 were significantly (*, p<0.005, 0.05 and 0.005, respectively) affected compared to control (Day 0). (B) Immunohistochemical detection of biotinylated $L.$ $esculentum$ lectin (1.0 mg/ml in 0.9% NaCl) in primary xenografts of human prostate tissue after injection of the lectin into the tail vein to visualize anastomosis and vascular integrity on Day 0 (control), and Day 1, Day 3, Day 7 and Day 14 after androgen deprivation. Bar: 30 μm.

To characterize further the effect of androgen deprivation on human prostate vascular integrity, changes in the diameter of vascular lumens and the leakage of serum constituents into the interstitial tissue space were evaluated in the human prostate xenograft model after androgen deprivation. Androgen deprivation was associated with a rapid and significant decrease ($p<0.05$) in lumen diameter of vessels, with the maximal decrease in vascular lumen diameter observed on Days 2-4 after androgen deprivation (FIG. 15A). However, vascular diameter started to increase by Days 4-5 after androgen deprivation, and reached pre-castration levels between Days 10-14 after androgen deprivation. The androgen deprivation-induced perturbation of vascular integrity was correlated temporally with leakage of serum proteins into the interstitial tissue space. The presence of fibrin/fibrinogen in the interstitial tissue space (FIG. 13B), and the leakage of systemically administered lectin through the compromised vasculature, peaked on Day 1 after androgen deprivation (FIG. 15B) and started to decrease on Day 3 after androgen deprivation, and ceased between Days 7-14 after androgen deprivation (FIG. 153B).

Increased VEGF-A Expression in Human Prostate Endothelial Cells Precedes Vascular Recovery After Androgen Deprivation. The rapid involution of human vascular endothelial cells in the prostate xenografts in response to androgen deprivation appeared to result from a loss of AR-mediated vascular signaling within vascular endothelial cells. However, the source of signaling that drove the rapid recovery of the vascular endothelial cell compartment in the absence of androgen signaling following androgen deprivation was unknown. The signals that induced endothelial cell proliferation could be autocrine, of endothelial cell origin, or be paracrine, originating from prostate stromal and/or epithelial cells within the tissue microenvironment.

Figure 16:
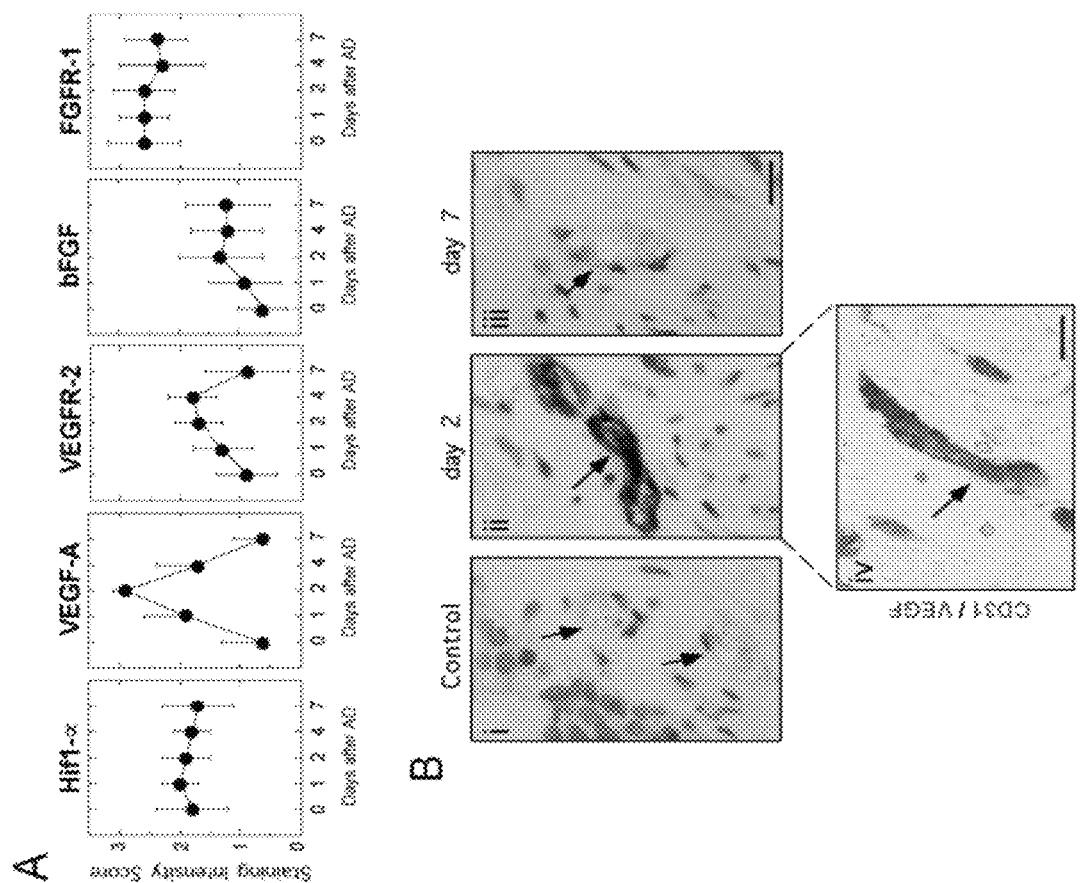
FIG. 16. VEGF-A expression after androgen deprivation in the short-term human prostate primary xenografts. (A) Immunostaining of HIF-1α, VEGF-A, VEGFR-2, bFGF and FGFR-1 in endothelial cells of human prostate xenografts was performed, and staining intensities were scored 0-3 using manual microscopy at 100×-400×. Data are averaged scores of two blinded investigators; changes in expression were evaluated for significance at 90% confidence, or greater. (B) Immunostaining for VEGF-A on Day 0 (i), Day 2 (ii), and Day 7 (iii) after androgen deprivation in prostate xenografts. Arrows indicate endothelial cells. (iv) VEGF-A and CD31 co-localization (arrow) confirmed the presence of VEGF-A in human prostate endothelial cells. Bars: 30 μm.

A semi-quantitative, IHC-based analysis of expression of signaling proteins and growth factors associated with vascular stabilization or angiogenesis was developed to characterize changes induced by androgen deprivation in the endothelial, epithelial and stromal cell compartments of the prostate xenografts. Immunohistochemical staining protocols were optimized for detection and localization of HIF-1α, VEGF-A, VEGFR-2, bFGF, FGFR-1, PDGF-AA, PDGF-BB, PDGFR-α, Ang-1, and Tie-2 protein. Several distinct temporal patterns of change in protein levels for genes associated with vascular homeostasis and angiogenesis were observed in response to androgen deprivation. HIF-1α was expressed at comparable levels in all 3 cellular compartments in prostate xenografts, and temporal changes in the protein levels after androgen deprivation were not observed (Table 1, FIG. 16A and Table 3). In contrast, VEGF-A, VEGFR-2 and bFGF protein levels demonstrated distinct temporal differences after androgen deprivation (Table 1, FIGS. 16A-B and Table 3). Endothelial cell up-regulation of expression of the angiogenesis-related proteins VEGF-A, and one of it's cognate receptors, VEGFR-2, was the most marked response of the prostate microenvironment to androgen deprivation. Expression of both VEGF-A and VEGFR-2 in endothelial cells peaked on Day 2 after androgen deprivation and returned to baseline levels on Day 7 (Table 1, FIG. 164A-B Table 3). The trend for the up-regulation of VEGF-A and VEGFR-2 was significant, with a 99% confidence level. A similar temporal pattern for VEGF-A expression, with a peak on Day 2, was observed in the stromal compartment, however, the magnitude of the up-regulation was smaller than that observed in the endothelial cell compartment. Confirmation of VEGF-A expression in human prostate endothelial cells in primary xenografts was demonstrated by co-localization of VEGF-A and CD31 protein (FIG. 164B-iv). In contrast to VEGF-A, bFGF protein levels increased from Day 0 to Day 2, and levels remained elevated through Day 7 (Table 1, FIG. 164A and Table 3). The trend observed for bFGF expression was significant at a 90% confidence level. In contrast, expression of VEGF-A, VEGFR-2 and bFGF in the epithelial compartments did not demonstrate temporal trends. FGFR-1 was expressed in all 3 cellular compartments in prostate xenografts, but demonstrated little temporal difference in expression in endothelium and epithelium. However, a significant temporal trend was observed in stromal cells, where staining intensity decreased after Day 2 (Table 3). In contrast, androgen deprivation did not induce significant temporal differences in expression of PDGF-AA, PDGF-BB, PDGFR-α, Ang-1 and Tie-2 in any of the prostate cellular compartments (Table 3). Taken together, these results demonstrate that androgen deprivation induced a temporally limited increase in the protein levels of VEGF-A, VEGFR-2 and bFGF in human prostate endothelial cells, which suggests an autocrine mechanism(s) for vascular stabilization and regrowth after removal of testicular androgen.

Figure 17:
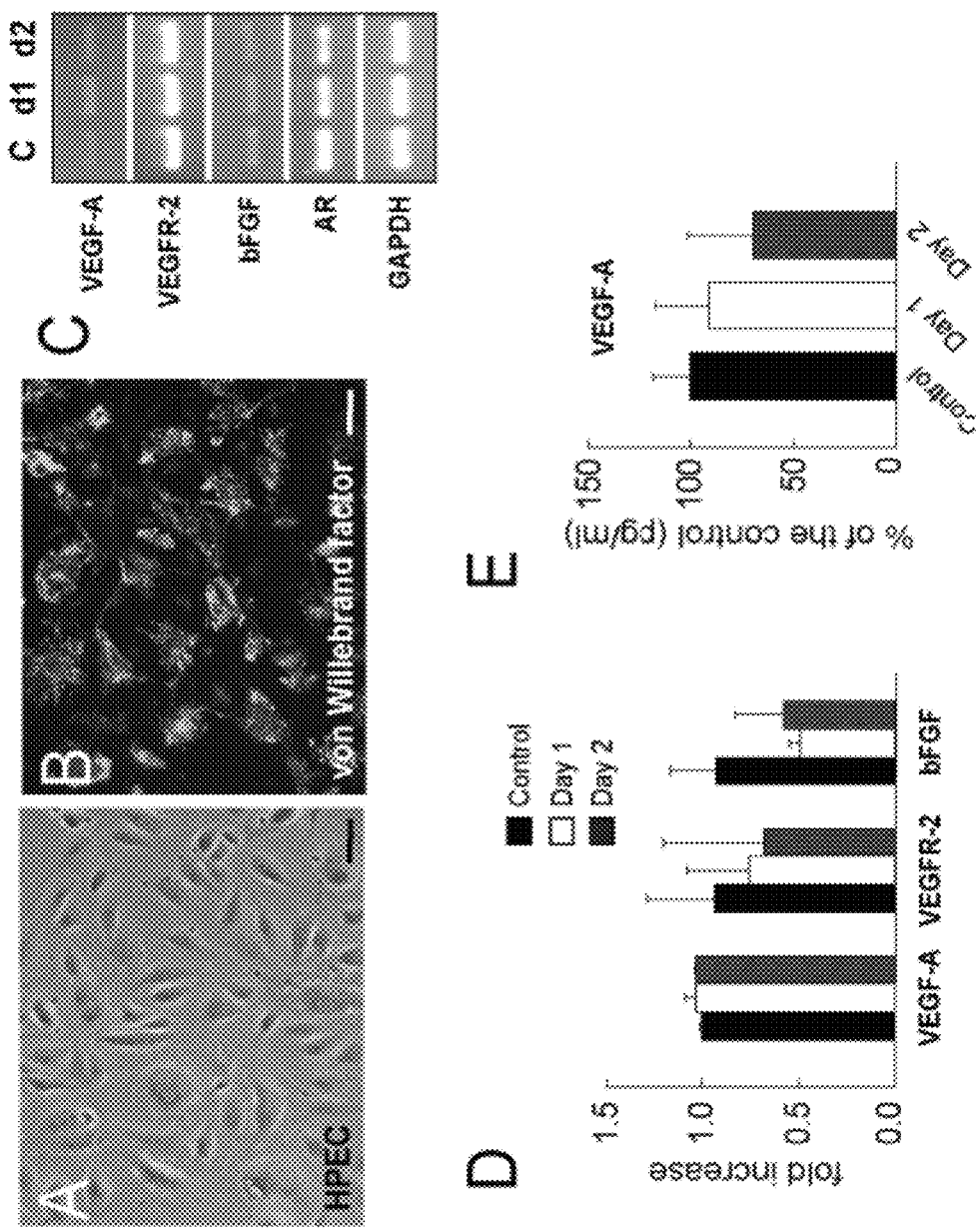
FIG. 17. Effect of androgen-deprivation on VEGF-A expression in primary cultures of human prostate endothelial cells. (A) HPEC in primary culture showed a typical cobblestone morphology as the cultures became confluent. Black bar: 25 μm. (B) Immunofluorescence analysis demonstrated that more than 95% of cells expressed von Willebrand Factor. White bar: 25 μm. (C) Primary cultures of HPEC were exposed to androgen deprivation by culturing the cells for 24 h (d1) and 48 h (d2) in endothelial cell growth media containing charcoal-stripped 5.0% FBS. Standard PCR analyses indicated that androgen deprivation induced a slight increase in VEGF-A mRNA, however, no effect was observed on VEGFR-2 and bFGF mRNA expression in primary cultures of HPEC. AR mRNA was slightly decreased after androgen deprivation (D). Standard PCR results were confirmed using quantitative real-time PCR. (E) Quantitative measurement by ELISA of VEGF-A protein levels in primary culture of human prostate endothelial cells showed no significant increase in VEGF-A after androgen deprivation (Day 1 and Day 2).

Androgen Deprivation Failed to Induce VEGF-A Expression In Primary Cultures of Human Prostate Endothelial Cells. The presence of functional AR in human prostate endothelial cells in vivo and in vitro, and the rapid up-regulation of VEGF-A in response to androgen deprivation, suggested AR could have a direct regulatory effect on VEGF-A expression in human prostate endothelial cells. To investigate if AR negatively regulated VEGF-A expression in prostate endothelial cells, primary cultures of HPEC established from fresh surgical specimens of human prostate using a Dynabead-based methodology were utilized to evaluate in vitro whether removal of testosterone stimulated up-regulated VEGF-A expression. Human prostate endothelial cells in primary culture showed endothelial cell morphology, functionality, and marker expression profiles comparable to HUVEC. Initially, human prostate endothelial cells in primary culture demonstrated an elongated appearance, which after 1 week in culture changed to a more typical cobblestone morphology of flattened cells as cultures became confluent (FIG. 17A). Immuno-cytochemical analyses using a specific antibody against von Willebrand Factor confirmed the purity of primary endothelial cell cultures, with more than 95% of the cells expressing von Willebrand Factor (FIG. 17B) with a granulated or punctate cytoplasmic pattern of localization, consistent with specific inclusion in Weibel-Palade bodies, a characteristic of endothelial cells.

Primary cultures of HPEC were subjected to androgen deprivation for 24 and 48 h, and to 24 h of androgen deprivation (charcoal-stripped FBS) followed by 24 h of replenishment of androgen (charcoal-stripped FBS supplemented with 1 nM DHT) to confirm that the increased VEGF-A expression in human prostate endothelial cells in response to androgen deprivation was a direct effect. Androgen deprivation induced a slight increase in VEGF-A mRNA expression in primary cultures of HPEC (FIG. 17C). However, no effect was observed in VEGFR-2 or bFGF mRNA (FIG. 17C). AR mRNA was slightly decreased after androgen deprivation, which confirmed the presence of AR in these cells and that androgen regulated AR expression mostly at the protein level through increasing AR protein stabilization. Real-time PCR was performed to validate the up-regulation in expression of VEGF-A mRNA induced by androgen deprivation. No changes in the levels of expression of VEGF-A, VEGFR-2 or bFGF mRNAs were apparent when normalized to GAPDH mRNA level (FIG. 17D). VEGF-A protein levels in HPEC were analyzed using ELISA to confirm that expression of VEGF-A was not affected in primary cultures of HPEC by androgen deprivation. No significant differences in the level of VEGF-A protein expression/secretion were apparent after androgen deprivation (FIG. 17E).

As can be seen from the foregoing description and the Figures, the human prostate primary xenografts represent a valuable model for translational research because the tissue retains all the components of the human prostate microenvironment, the in vivo tissue architecture and human pathophysiology, and androgen responsiveness. This unique model has provided three important new observations of the human prostate tissue microenvironment: 1) there is a transient, short window (4-7 days) immediately following androgen deprivation in which the integrity of the prostate microvasculature is compromised; 2) androgen-sensitive human endothelial cells rapidly develop an alternative mechanism(s) for maintaining homeostasis and regenerating the microvascular network in the absence of androgen; and 3) androgen deprivation results in up-regulation of VEGF-A by specifically the prostate endothelial cells, potentially creating autocrine-mediated growth that would be insensitive to anti-VEGF therapy. A comparable androgen independent revascularization was not observed in rat prostate. The difference in the response of rat prostate and the human prostate tissue xenografts could result in missed opportunities for identification of more effective treatments for BPH or advanced CaP. It is believed that the transient window of vascular perturbation presents an optimal timeframe for the administration of therapeutic modalities that target prostate cancer epithelial cells with enhanced therapeutic efficacy, or of anti-angiogenic adjuvant therapies focused on preventing the restoration of microvascular integrity.

TABLE 1

Table 1. IHC analysis of angiogenesis factor and growth factor protein levels in the three prostate cellular compartments in primary prostate tissue xenografts.

| Sheet | Table | p_hat | Mack_Wolfe Statistic Value | p_value |
|---|---|---|---|---|
| HIF-1 alpha | Epithelium | 5 | 0.967 | >0.2 |
|  | Endothelium | 2 | 1.632 | >0.2 |
|  | Stroma | 5 | 0.370 | >0.2 |
| VEGF-A | Epithelium | 4 | 0.556 | >0.2 |
|  | Endothelium | 3 | 4.652 | <0.02*** |
|  | Stroma | 3 | 2.326 | 0.087 |
| VEGFR-2 | Epithelium | 2 | 1.459 | >0.2 |
|  | Endothelium | 3 | 3.376 | <0.02*** |
|  |  | 4 | 3.664 | <0.02*** |
|  | Stroma | 4 | 1.025 | >0.2 |
| Ang-1 | Epithelium | 2 | 0.608 | >0.2 |
|  |  | 4 | 0.365 | >0.2 |
|  | Endothelium | 3 | 1.276 | >0.2 |
|  | Stroma | 1 | 1.488 | >0.2 |
| Tie-2 | Epithelium |  | all obs = 0 |  |
|  | Endothelium | 3 | 0.563 | >0.2 |
|  | Stroma | 5 | 1.943 | >0.2 |
| bFGF | Epithelium | 3 | 1.011 | >0.2 |
|  | Endothelium | 3 | 1.557 | >0.2 |
|  |  | 4 | 2.101 | 0.148 |
|  | Stroma | 2 | 0.399 | >0.2 |
| FGFR-1 | Epithelium | 4 | 1.244 | >0.2 |
|  | Endothelium | 1 | 0.906 | >0.2 |
|  | Stroma | 3 | 2.138 | 0.135 |
| PDGF-AA | Epithelium | 5 | 1.321 | >0.2 |
|  | Endothelium | 3 | 0.957 | >0.2 |
|  | Stroma | 3 | 1.951 | >0.2 |
| PDGF-BB | Epithelium |  | all obs = 0 |  |
|  | Endothelium | 2 | 1.007 | >0.2 |
|  | Stroma | 3 | 0.919 | >0.2 |

TABLE 1-continued

Table 1. IHC analysis of angiogenesis factor and growth factor protein levels in the three prostate cellular compartments in primary prostate tissue xenografts.

| Sheet | Table | p_hat | Mack_Wolfe Statistic Value | p_value |
|---|---|---|---|---|
| PDGFR-alpha | Epithelium | 4 | 0.208 | >0.2 |
| | Endothelium | 4 | 0.254 | >0.2 |
| | Stroma | 5 | 1.187 | >0.2 |

Mack-Wolfe Statistical Analysis of the data presented in tabular form, with critical Mack_Wolfe Statistic Value for 99%, 95% and 90% confidence limits provided for reference (p, 0.01, p, 0.05, and p, 0.10).
(Significant Trend, p < 0.02, indicated by *; Approaching Significance, p < 0.10, indicated by ; Trend of Interest, p < 0.20, indicated by *; see Table 3).
Critical values: A* p, 0.01 = 2.761, A* p, 0.05 = 2.240, A* p, 0.10 = 1.951
*Vector Laboratories, Inc., Burlingame, CA
+ Lab Vision, Corp.
− NeoMarkers, Fremont, CA

TABLE 2

Statistical Summary of Vessel, Epithelial and Stromal Analysis

| Post-CX | 0-1 | 0-2 | 0-4 | 0-7 | 1-2 | 1-4 | 1-7 | 2-4 | 2-7 | 4-7 |
|---|---|---|---|---|---|---|---|---|---|---|
| MVD | 0.1551 | 0.2480 | 0.4597 | 0.8144 | 0.9065 | 0.5198 | 0.1402 | 0.4196 | 0.3105 | 0.5737 |
| VeAI | 0.0156 | 0.0001 | 0.0752 | 0.4787 | 0.0078 | 0.0781 | 0.1484 | 0.00007 | 0.0022 | 0.3853 |
| VePI | 0.0770 | 0.1094 | 0.0097 | 0.0562 | 0.0156 | 0.0055 | 0.0145 | 0.4609 | 0.9375 | 0.1848 |
| EpAI | 0.1476 | 0.2116 | 0.0762 | 0.0803 | 0.6019 | 0.5096 | 0.1764 | 0.7966 | 0.2325 | 0.2771 |
| EpPI | 0.4677 | 0.5795 | 0.4523 | 0.9073 | 0.2409 | 0.1608 | 0.4898 | 0.8536 | 0.7408 | 0.6425 |
| StAI | 0.0784 | 0.7230 | 0.8012 | 0.0827 | 0.4196 | 0.0371 | 0.0028 | 0.4312 | 0.0299 | 0.0052 |
| StPI | 0.0028 | 0.0307 | 0.5469 | 0.7691 | 0.0040 | 0.0234 | 0.0033 | 0.3828 | 0.1637 | 0.5781 |
| Symbols | + | ++ | +++ | ++++ | # | ## | ### | * | ** | ^ |

2-Day Paired Analysis of Changes After Castration
P Values from Paired t-Tests and Wilcoxon Signed Rank Tests (Italics)
Family Wise Analysis ($\alpha = 0.005$, $P < 0.005$) highlighted;
Pair Wise Analysis ($\alpha = 0.05$, $P < 0.05$) boxed
Symbols (+, ++, +++, ++++, #, ##, ###, *, **, ^) represent day pairings found to be statistically significant.

TABLE 3

Mack-Wolfe Analysis (Two-Sided Unimodal Test Results)
Mack_Wolfe Analysis
Two-Sided Unimodal Test Results

| Sheet | Table | p_hat | Statistic Value | p_value | Trend |
|---|---|---|---|---|---|
| Ar | Epithelium | 4 | 1.719 | >0.2 | |
| | Endothelium | 4 | 3.473 | <0.02 | DDDU |
| | Stroma | 3 | 2.288 | 0.093 | |
| ER-α | Epithelium | 3 | 1.107 | >0.2 | |
| | Endothelium | 5 | 1.406 | >0.2 | |
| | Stroma | 2 | 0.174 | >0.2 | |
| | Stroma | 4 | 0.729 | >0.2 | |
| | Stroma | 5 | 0.936 | >0.2 | |
| ER-β | Epithelium | 3 | 0.713 | >0.2 | |
| | Endothelium | 4 | 0.521 | >0.2 | |
| | Stroma | 3 | 0.563 | >0.2 | |
| HIF-1α | Epithelium | 5 | 0.967 | >0.2 | |
| | Endothelium | 2 | 1.632 | >0.2 | |
| | Stroma | 5 | 0.370 | >0.2 | |
| VEGF | Epithelium | 4 | 0.556 | >0.2 | |
| | Endothelium | 3 | 4.652 | <0.02 | UUDD |
| | Stroma | 3 | 2.326 | 0.087 | |
| Ang-1 | Epithelium | 2 | 0.608 | >0.2 | |
| | | 4 | 0.365 | >0.2 | |
| | Endothelium | 3 | 1.276 | >0.2 | |
| | Stroma | 1 | 1.488 | >0.2 | |
| VEGFR-2 | Epithelium | 2 | 1.459 | >0.2 | |
| | Endothelium | 3 | 3.376 | <0.02 | UUDD |
| | Endothelium | 4 | 3.664 | <0.02 | UUUD |
| | Stroma | 4 | 1.025 | >0.2 | |
| Tie-2 | Epithelium | | No staining observed | | |
| | Endothelium | 3 | 0.563 | >0.2 | |
| | Stroma | 3 | 1.943 | >0.2 | |
| bFGF | Epithelium | 3 | 1.011 | >0.2 | |
| | Endothelium | 3 | 1.557 | >0.2 | |
| | Endothelium | 4 | 2.101 | 0.148 | |
| | Stroma | 2 | 0.399 | >0.2 | |
| FGFR-1 | Epithelium | 4 | 1.244 | >0.2 | |
| | Endothelium | 1 | 0.906 | >0.2 | |
| | Stroma | 3 | 2.138 | 0.135 | |
| PDGF-AA | Epithelium | 5 | 1.321 | >0.2 | |
| | Endothelium | 3 | 0.957 | >0.2 | |
| | Stroma | 3 | 1.951 | >0.2 | |
| PDGF-BB | Epithelium | | No staining observed | | |
| | Endothelium | 2 | 1.007 | >0.2 | |
| | Stroma | 3 | 0.919 | >0.2 | |
| PDGFR-α | Epithelium | 4 | 0.208 | >0.2 | |
| | Endothelium | 4 | 0.254 | >0.2 | |
| | Stroma | 5 | 1.187 | >0.2 | |

Critical values: $A^*_{p,.01} = 2.761$, $A^*_{p,.05} = 2.240$, $A^*_{p,.10} = 1.951$

Bold = Trend of Interest, >90% Confidence

☐ = Approaching Significance, 95% confindence

▒ = Significant, 99% Confidence

While specific examples have been presented herein, those skilled in the art will recognize that routine modifications can be made to the invention as described herein and these modifications are intended to be within the scope of the invention.

We claim:

1. A method for treating an individual for human prostate cancer comprising the steps of:
   i) initiating androgen deprivation in the individual, wherein the initiating androgen deprivation is performed by administration of an anti-androgenic agent selected from the group consisting of leuprolide, goserelin, triptorelin, flutamide, bicalutamide, nilutamide, and combinations thereof; and
   ii) administering docetaxel to the individual within 1-7 days of initiating androgen deprivation;
   wherein the administration of step ii) reduces the number of blood vessels, and/or induces death of vascular endothelial cells, epithelial cells, or prostate cancer epithelial cells, or combinations thereof, in the prostate of the individual.

2. The method of claim 1 further comprising ceasing androgen deprivation in the individual for a period of time and subsequently repeating steps i) and ii).

3. The method of claim 1, wherein the death is induced by apoptosis.

* * * * *